(12) United States Patent
Palepu

(10) Patent No.: US 7,772,274 B1
(45) Date of Patent: Aug. 10, 2010

(54) DOCETAXEL FORMULATIONS WITH LIPOIC ACID

(75) Inventor: Nagesh Palepu, Southampton, PA (US)

(73) Assignee: Scidose, LLC, Amherst, MA (US)

( * ) Notice: Subject to any disclaimer, the term of this patent is extended or adjusted under 35 U.S.C. 154(b) by 0 days.

(21) Appl. No.: 12/721,563

(22) Filed: Mar. 11, 2010

Related U.S. Application Data

(63) Continuation-in-part of application No. 12/589,145, filed on Oct. 19, 2009.

(51) Int. Cl.
A61K 31/337 (2006.01)

(52) U.S. Cl. ..................................................... 514/449

(58) Field of Classification Search .................. 514/449
See application file for complete search history.

(56) References Cited

U.S. PATENT DOCUMENTS

| | | | |
|---|---|---|---|
| 4,814,470 A | 3/1989 | Colin et al. | |
| 5,403,858 A | 4/1995 | Bastard et al. | |
| 5,438,072 A | 8/1995 | Bobee et al. | |
| 5,698,582 A | 12/1997 | Bastart et al. | |
| 5,714,512 A | 2/1998 | Bastart et al. | |
| 5,750,561 A | 5/1998 | Bastart et al. | |
| 5,968,972 A | 10/1999 | Broder et al. | |
| 6,071,952 A | 6/2000 | Owens et al. | |
| 6,136,846 A | 10/2000 | Rubinfeld et al. | |
| 6,153,644 A | 11/2000 | Owens et al. | |
| 6,245,805 B1 | 6/2001 | Broder et al. | |
| 6,319,943 B1 | 11/2001 | Joshi et al. | |
| 6,395,770 B1 | 5/2002 | Broder et al. | |
| 6,458,373 B1 | 10/2002 | Lambert et al. | |
| 6,479,540 B1 | 11/2002 | Constantinides et al. | |
| 6,509,370 B1 | 1/2003 | Joshi-Hangal et al. | |
| 6,531,139 B1 | 3/2003 | Gao et al. | |
| 6,610,735 B2 | 8/2003 | Broder et al. | |
| 6,660,286 B1 | 12/2003 | Lambert et al. | |
| 6,667,048 B1 | 12/2003 | Lambert et al. | |
| 6,727,280 B2 | 4/2004 | Palepu et al. | |
| 6,730,698 B2 | 5/2004 | Broder et al. | |
| 6,818,615 B2 | 11/2004 | Broder et al. | |
| 6,936,583 B2 | 8/2005 | Broder et al. | |
| 6,964,946 B1 | 11/2005 | Gutierrez-Rocca et al. | |
| 6,979,456 B1 | 12/2005 | Parikh et al. | |
| 6,982,282 B2 | 1/2006 | Lambert et al. | |
| 7,030,155 B2 | 4/2006 | Lambert et al. | |
| 7,041,640 B2 | 5/2006 | Broder et al. | |
| 7,115,565 B2 | 10/2006 | Gao et al. | |
| 7,223,770 B2 | 5/2007 | Zhang et al. | |
| 7,618,975 B2 | 11/2009 | Cai et al. | |
| 2002/0049158 A1 | 4/2002 | Woo et al. | |
| 2002/0102280 A1 | 8/2002 | Anderson | |
| 2002/0156125 A1 | 10/2002 | Broder et al. | |
| 2003/0027858 A1 | 2/2003 | Lambert et al. | |
| 2003/0087954 A1 | 5/2003 | Palepu et al. | |
| 2003/0105156 A1 | 6/2003 | Palepu et al. | |
| 2003/0109575 A1 | 6/2003 | Lambert et al. | |
| 2003/0147959 A1 | 8/2003 | Lambert et al. | |
| 2003/0170279 A1 | 9/2003 | Lambert et al. | |
| 2004/0022820 A1 | 2/2004 | Anderson | |
| 2004/0053993 A1 | 3/2004 | Constantinides et al. | |
| 2004/0127551 A1 | 7/2004 | Zhang et al. | |
| 2004/0202712 A1 | 10/2004 | Lambert et al. | |
| 2005/0004002 A1 | 1/2005 | Desai et al. | |
| 2005/0119340 A1 | 6/2005 | Anderson et al. | |
| 2005/0142189 A1 | 6/2005 | Lambert et al. | |
| 2005/0148534 A1 | 7/2005 | Castellino et al. | |
| 2005/0152979 A1 | 7/2005 | Besman et al. | |
| 2005/0187147 A1 | 8/2005 | Newman et al. | |
| 2005/0232952 A1 | 10/2005 | Lambert et al. | |
| 2005/0238634 A1 | 10/2005 | Broder et al. | |
| 2005/0267201 A1 | 12/2005 | Gutierez-Rocca et al. | |
| 2005/0272806 A1 | 12/2005 | Falotico et al. | |
| 2006/0003002 A1 | 1/2006 | Fikstad et al. | |
| 2006/0003976 A1 | 1/2006 | Zhang et al. | |

(Continued)

FOREIGN PATENT DOCUMENTS

| | | |
|---|---|---|
| KR | 10-2010-0018741 | 2/2010 |
| WO | 00/78247 | 12/2000 |
| WO | 01/72299 | 10/2001 |
| WO | 01/72300 | 10/2001 |
| WO | 02/26208 | 4/2002 |
| WO | 02/092077 | 11/2002 |
| WO | 03/057208 | 7/2003 |
| WO | 03/074027 | 9/2003 |

(Continued)

OTHER PUBLICATIONS

TAXOTERE® Prescribing Information, Nov. 2008.
International Search Report and Written Opinion of the International Search Authority dated Sep. 3, 2008 in corresponding PCT/US2008/007619.
Eriox Product Literature, Nov. 2007.

*Primary Examiner*—James D Anderson
(74) *Attorney, Agent, or Firm*—Frommer Lawrence & Haug LLP; Sandra Kuzmich; Russell A. Garman

(57) ABSTRACT

Pharmaceutical formulations comprising docetaxel, solubilizer, and α-lipoic acid, wherein the formulation is substantially free of polysorbates and polyethoxylated castor oil. The solubilizer may comprise glycofurol, acetic acid, benzyl alcohol, or ethanol. The α-lipoic acid, at certain concentrations, may impart stability and prevent degradation of docetaxel while the formulations are in storage. The formulations may be combined with a diluent, which comprises one or more hydrotropes such as tocopherol polyethylene glycol succinate and polyethylene glycol. The formulations combined with the diluent also exhibit stability after storage. Methods of administering docetaxel comprise preparing the formulation comprising docetaxel, solubilizer, and α-lipoic acid; mixing the formulation with a diluent; diluting the resulting formulation in saline, water for injection, or the like; and then injecting the formulations into patients in need thereof.

20 Claims, 2 Drawing Sheets

U.S. PATENT DOCUMENTS

| | | |
|---|---|---|
| 2006/0024360 A1 | 2/2006 | Chen |
| 2006/0172014 A1 | 8/2006 | Curd et al. |
| 2006/0188566 A1 | 8/2006 | Liversidge et al. |
| 2006/0189679 A1 | 8/2006 | Holton et al. |
| 2006/0223760 A1 | 10/2006 | Li et al. |
| 2006/0229359 A1 | 10/2006 | Zhang et al. |
| 2006/0234909 A1 | 10/2006 | Newman et al. |
| 2006/0263434 A1 | 11/2006 | Desai et al. |
| 2006/0292186 A1 | 12/2006 | Garrigue et al. |
| 2007/0060635 A1 | 3/2007 | Broder et al. |
| 2007/0082838 A1 | 4/2007 | De et al. |
| 2007/0116729 A1 | 5/2007 | Palepu et al. |
| 2007/0117744 A1 | 5/2007 | Desai et al. |
| 2007/0128289 A1 | 6/2007 | Zhao |
| 2007/0128290 A1 | 6/2007 | Desai et al. |
| 2007/0141093 A1 | 6/2007 | Zhang et al. |
| 2007/0166388 A1 | 7/2007 | Desai et al. |
| 2007/0207173 A1 | 9/2007 | Chen |
| 2007/0207196 A1 | 9/2007 | Zhang |
| 2007/0208044 A1 | 9/2007 | Cai et al. |
| 2007/0244113 A1 | 10/2007 | Cai et al. |
| 2007/0244114 A1 | 10/2007 | Cai et al. |
| 2007/0249601 A1 | 10/2007 | Cai et al. |
| 2007/0281934 A1 | 12/2007 | Buggy et al. |
| 2008/0146651 A1 | 6/2008 | Jee et al. |
| 2008/0319048 A1 | 12/2008 | Palepu et al. |
| 2009/0215882 A1 | 8/2009 | Bouzada et al. |
| 2009/0215883 A1 | 8/2009 | Bouzada et al. |
| 2009/0227549 A1 | 9/2009 | Palepu et al. |
| 2009/0318543 A1 | 12/2009 | Vu et al. |
| 2010/0015195 A1 | 1/2010 | Jain et al. |

FOREIGN PATENT DOCUMENTS

| | | |
|---|---|---|
| WO | 2005/020962 | 3/2005 |
| WO | 2005/039554 | 5/2005 |
| WO | 2005/097105 | 10/2005 |
| WO | 2006/133510 | 12/2006 |
| WO | 2007/020085 | 2/2007 |
| WO | 2008/026048 | 3/2008 |
| WO | 2008/042841 | 4/2008 |
| WO | 2009/002425 | 12/2008 |
| WO | 2009/090614 | 7/2009 |

DOCETAXEL FORMULATIONS WITH LIPOIC ACID

CROSS REFERENCE TO RELATED APPLICATIONS

This application is a continuation-in-part of U.S. patent application Ser. No. 12/589,145, filed on Oct. 19, 2009.

FIELD OF THE INVENTION

The present invention relates to pharmaceutical formulations comprising docetaxel, a solubilizer, and α-lipoic acid, wherein the formulation is substantially free of polysorbates and polyethoxylated castor oil. The present invention also relates to pharmaceutical formulations comprising docetaxel, a solubilizer, α-lipoic acid, and a diluent. The diluent may comprise one or more hydrotropes. In addition, the present invention relates to pharmaceutical formulations comprising docetaxel, a solubilizer, α-lipoic acid, a diluent, and a solution for injection. Furthermore, the present invention relates to methods for administering docetaxel to patients in need thereof and for preparing the pharmaceutical formulations.

BACKGROUND OF THE INVENTION

Antineoplastic agents inhibit and combat the development of neoplasms, which are abnormal masses of tissue resulting from irregular proliferation of cells. One such antineoplastic agent is docetaxel, a taxane compound derived from the renewable needle biomass of yew plants. Docetaxel binds to free tubulin and promotes the assembly of microtubules, which reduces the availability of tubulin for, and thereby prevents, cell division. Simultaneously, docetaxel inhibits microtubule disassembly, causing apoptosis. See TAXOTERE® Prescribing Information.

Docetaxel is marketed as TAXOTERE®, which is FDA-approved for breast cancer, non-small cell lung cancer, hormone refractory prostate cancer, gastric adenocarcinoma, and squamous cell carcinoma of head and neck cancer. TAXOTERE® is available as an injection concentrate in single-dose vials containing 40 mg/mL docetaxel (on an anhydrous basis) and 1040 mg/mL polysorbate 80 (also known as TWEEN 80®). TAXOTERE® is provided as an injection concentrate and requires dilution to 10 mg/mL prior to use. Hence, a sterile, non-pyrogenic, single-dose diluent containing 13% ethanol in water for injection is supplied in a separate vial. After dilution, the required amount of docetaxel is then transferred from the 10 mg/mL initial diluted solution to an infusion bag or bottle of either 0.9% sodium chloride solution or 5% dextrose solution to produce a final dilution for infusion having a concentration of 0.3 to 0.74 mg/mL. The recommended therapy is six cycles of docetaxel given once every three weeks. See id.

The presence of polysorbate 80 in TAXOTERE®, however, most often results in serious side effects. Such reactions characterized by generalized rash/erythema, hypotension and/or bronchospasm, or very rarely fatal anaphylaxis, have been reported in patients. Hypersensitivity reactions require immediate discontinuation of the TAXOTERE® infusion and administration of appropriate therapy.

In order to reduce the side effects induced by polysorbate 80, patients are treated with dexamethasone for three days prior to therapy. Dexamethasone is a steroid that suppresses the immune response in patients, which can be especially detrimental in cancer patients under chemotherapy, whose immunity may already be compromised due to the destruction of healthy cells by the chemotherapeutic treatment. As a result, these patients can be susceptible to bacterial and fungal infections. Further, despite receiving the recommended 3-day dexamethasone premedication, patients still report hypersensitivity side effects from TAXOTERE®.

Due to these side effects, most of the patients stop TAXOTERE® therapy by the end of the second or third cycle, skip a dose, or continue further therapy at a reduced dose. Similarly, other solubilizing agents such as CREMOPHOR EL®, which is a polyethoxylated castor oil used in connection with the marketed paclitaxel product TAXOL®, induce similar allergic reactions requiring premedication with a steroid.

Therefore, a new formulation of docetaxel is needed to avoid these side effects, premedication requirements, and patient noncompliance issues associated with the currently marketed formulation of TAXOTERE®.

SUMMARY OF THE INVENTION

Applicant has developed stable formulations of docetaxel injection concentrate (sometimes referred to as the initial concentrate), docetaxel initial diluted solution (sometimes referred to as the intermediate concentrate), and docetaxel final dilution for infusion (sometimes referred to as the final concentrate); a kit comprising the docetaxel injection concentrate and a diluent for preparing the docetaxel initial diluted solution; and methods for administering docetaxel to patients in need thereof and for preparing the docetaxel formulations.

Therefore, an aspect of the present invention may relate to a pharmaceutical formulation (e.g., an injection concentrate) for use in treatment of a patient in need thereof, comprising: (a) docetaxel, or a pharmaceutically acceptable salt thereof, in an amount of about 40 to about 80 mg/mL; (b) glycofurol; and (c) α-lipoic acid, or a pharmaceutically acceptable salt thereof, in an amount of about 1 mg/mL to about 20 mg/mL. The formulation may be substantially free of polysorbates and polyethoxylated castor oil. The total peak area % of unknown impurities may be less than about 0.75% as measured by high performance liquid chromatography ("HPLC") after storage at 40° C. over 1 month.

In certain embodiments of this pharmaceutical formulation (e.g., an injection concentrate), docetaxel, or a pharmaceutically acceptable salt thereof, may be in an amount of about 80 mg/mL In some embodiments, α-lipoic acid, or a pharmaceutically acceptable salt thereof may be in an amount of about 2 mg/mL, about 5 mg/mL, about 7.5 mg/mL or about 10 mg/mL and no unknown impurity may be present in an amount greater than 0.2% as measured by HPLC after storage at 40° C. over 1 month. In further embodiments, α-lipoic acid, or a pharmaceutically acceptable salt thereof may be in an amount of about 5 mg/mL and no unknown impurity may be present in an amount greater than 0.2% as measured by HPLC after storage at 40° C. over 3 months.

In some embodiments of this pharmaceutical formulation (e.g., an injection concentrate), α-lipoic acid, or a pharmaceutically acceptable salt thereof may be in an amount of about 5 mg/mL to about 20 mg/mL and the total peak area % of impurities may be less than about 2% as measured by HPLC after storage at 40° C. over 3 months. In particular embodiments, α-lipoic acid, or a pharmaceutically acceptable salt thereof is in an amount of about 5 mg/mL to about 20 mg/mL and wherein the total peak area % of unknown impurities is no greater than about 1% as measured by HPLC after storage at 40° C. over 3 months.

In some embodiments of this pharmaceutical formulation (e.g., an injection concentrate), the percent of initial concentration of docetaxel may be no less than about 91% as measured by HPLC after storage at 40° C. for 3 months.

Another aspect of the present invention may relate to a pharmaceutical formulation (e.g., initial diluted solution) for use in treatment of a patient in need thereof, comprising: (a) docetaxel, or a pharmaceutically acceptable salt thereof; (b) glycofurol; (c) α-lipoic acid, or a pharmaceutically acceptable salt thereof, in an amount of about 0.125 to about 2.5 mg/mL; and (d) a diluent. The formulation may be substantially free of polysorbates and polyethoxylated castor oil. Also, the physical appearance of the formulation may be clear after 24 hours at room temperature.

In several embodiments of this pharmaceutical formulation (e.g., initial diluted solution), the diluent may comprise at least one hydrotrope. In particular embodiments, the hydrotrope may be tocopherol polyethylene glycol succinate ("TPGS"), polyethylene glycol ("PEG") 400, or both TPGS and PEG 400. In certain embodiments, the diluent may comprise about 0.625 mg/mL α-lipoic acid, or a pharmaceutically acceptable salt thereof, about 1.5 grams TPGS, about 2.5 mL PEG 400, and may further comprise about 72 mg sodium chloride. In some embodiments, the % of initial concentration of docetaxel in the initial diluted solution may be about 99% as measured by high performance liquid chromatography after storage for 24 hours at room temperature; in further embodiments, the total peak area % of impurities may be less than about 1% as measured by high performance liquid chromatography after 24 hours at room temperature; in yet further embodiments, the peak area % of any individual impurity may be below detectable levels as determined by high performance liquid chromatography after 24 hours at room temperature. In even further embodiments, docetaxel may be in an amount about 0.32 mg/mL to 0.74 mg/mL after final dilution with saline, dextrose or water, and after about 8 hours at room temperature the physical appearance of the formulation is clear.

Yet, another aspect of the present invention relates to a package comprising: (a) a pharmaceutical formulation comprising (i) docetaxel, or a pharmaceutically acceptable salt thereof, in an amount of about 40 to about 80 mg/mL; (ii) glycofurol; and (iii) α-lipoic acid, or a pharmaceutically acceptable salt thereof, in an amount of about 1 to about 20 mg/mL; and (b) a diluent comprising at least one hydrotrope. The pharmaceutical formulation and the diluent may be substantially free of polysorbates and polyethoxylated castor oil.

In certain embodiments of this package, the hydrotrope may be tocopherol polyethylene glycol succinate (TPGS), polyethylene glycol (PEG), or both TPGS and PEG. In particular embodiments, the total peak area % of unknown impurities in the docetaxel solution may be no greater than about 0.75% as measured by high performance liquid chromatography after storage at 40° C. over 1 month.

In further embodiments of this package, (i) the pharmaceutical formulation may comprise docetaxel in an amount of about 80 mg; α-lipoic acid in an amount of about 5 mg; and glycofurol in an amount sufficient to bring the volume of the pharmaceutical formulation to about 1 mL; and (ii) the diluent may comprise tocopherol polyethylene glycol succinate (TPGS) in an amount of about 1.5 g, polyethylene glycol 400 in an amount of about 2.5 mL, sodium chloride in an amount of about 72 mg, and water in an amount sufficient to bring the diluent volume to about 7 mL.

Moreover, an aspect of the present invention relates to a method for preparing docetaxel. In certain embodiments, the method may comprise mixing one or more solubilizers, α-lipoic acid and docetaxel. In some embodiments, the resulting formulation may be an injection concentrate. In particular embodiments, the injection concentrate may be mixed with a diluent. In further embodiments, the resulting formulation may be an initial diluted solution. In yet further embodiments, the initial diluted solution may be mixed with an infusion solution. In even further embodiments, the resulting solution is a final dilution for infusion.

In some embodiments of this method, the final dilution for infusion may be administered to the patient. In certain embodiments, the administration of the final dilution for infusion may not require premedication.

These and other embodiments are disclosed or are obvious from and encompassed by, the following Detailed Description.

BRIEF DESCRIPTION OF THE DRAWINGS

For a more complete understanding of the invention, reference is made to the following description and accompanying drawings, in which.

DETAILED DESCRIPTION

Figure 1:
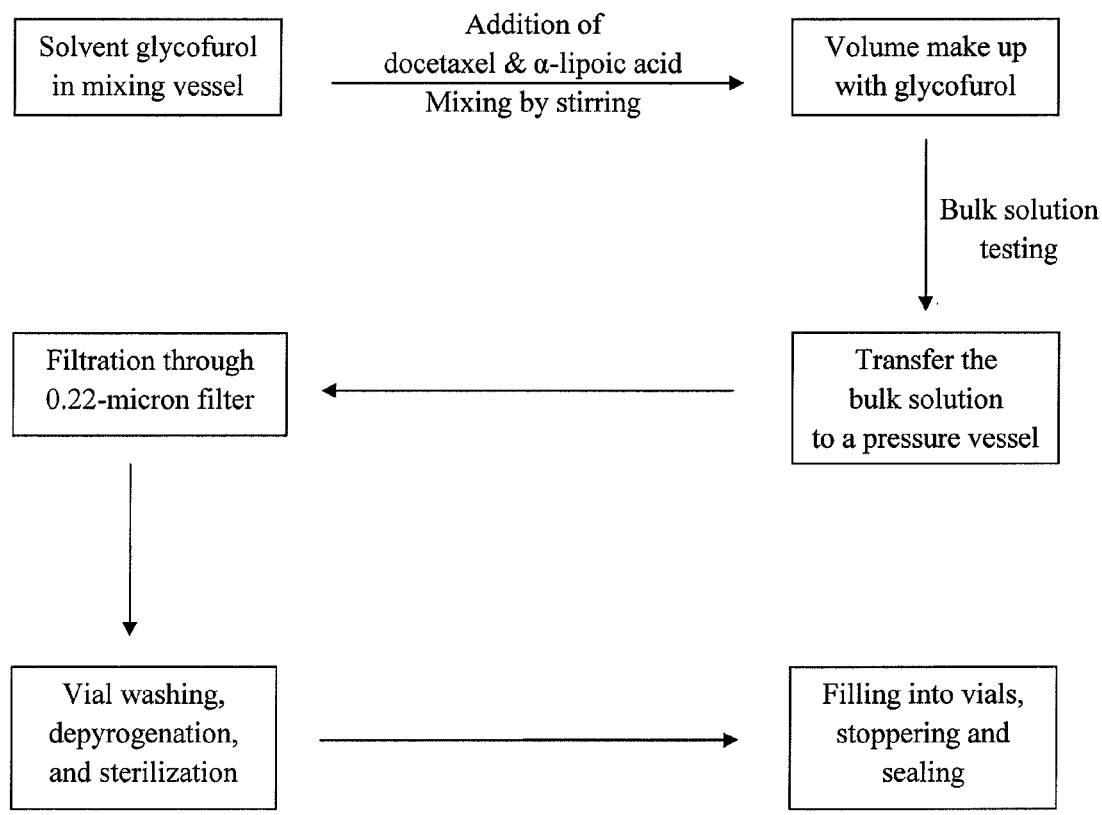
FIG. 1 is a flow diagram showing steps for preparing an injection concentrate according to an embodiment of the invention.

The present invention is directed to formulations of docetaxel injection concentrate, docetaxel initial diluted solution, and docetaxel final dilution for infusion; a kit comprising the docetaxel injection concentrate and a diluent for preparing the docetaxel initial diluted solution; and methods for administering docetaxel to patients in need thereof and for preparing the docetaxel formulations.

Docetaxel is classified as a taxane, a class of compounds that can eradicate cancer cells. This class of compounds is virtually insoluble in water, thereby making it difficult to formulate taxanes for intravenous administration to patients. Since taxanes are cytotoxic, these compounds must be diluted before administrating to patients. Thus, a formulator's challenge not only encompasses solubilizing the taxane, but also includes preventing the taxane from precipitating after it is diluted for intravenous ("IV") infusion and during administration into the patient's bloodstream. Due to such challenges, a formulator must select excipients that will solubilize the taxane and prevent it from precipitating upon subsequent dilution. Furthermore, these selected excipients must allow the taxane to be administered by the IV route to a patient safely and effectively, with minimal side effects. To this end, Applicant sought to develop a formulation that solubilized docetaxel, prevented its precipitation upon dilution, and avoided the use of polysorbates and polyethoxylated castor oil, which as described above most often induce side effects in patients and require premedication.

As a result, Applicant studied the solubility of docetaxel in several solvents as illustrated in Example 1. The results indicate that TPGS 1000, benzyl alcohol, acetic acid, ethanol, and glycofurol were comparable or superior to TWEEN 80® and TWEEN 20® with respect to solubilizing docetaxel.

Applicant then explored the stability of docetaxel when formulated with glycofurol, and compared it to the stability of TAXOTERE®, as seen in Example 2. Injection concentrates were prepared comprising 80 mg of docetaxel and glycofurol that was q.s. to either 1 mL (resulting in a concentration of 80 mg/mL) or 2 mL (resulting in a concentration of 40 mg/mL). See Example 2. Comparing the stability of the 80 mg/mL and 40 mg/mL docetaxel injection concentrates to TAXO- TERE®, Applicant recognized that the total peak area % of impurities in TAXOTERE® was less after storage at 40° C. for 3 months as compared to the total peak area % of impurities in either injection concentrate. See Example 2. Applicant also observed that the known impurities 10-oxo-docetaxel, 7-hydroxy-epi-docetaxel, and 7-epi-10-oxo-docetaxel, which are oxidative degradants, contributed mostly to this difference. As these degradants are generated via an oxidation pathway, Applicant considered including an antioxidant in the injection concentrate to reduce the generation of these known degradants.

Applicant also noted that the impurity profiles for the injection concentrate comprising about 80 mg/mL docetaxel and glycofurol after storage at 40° C. for up to 3 months were similar to the impurity profiles for the injection concentrate comprising about 40 mg/mL docetaxel and glycofurol at 40° C. up to 3 months. See Example 2. Based on these results, Applicant determined that the drug-to-solvent ratio did not, in general, adversely affect the solution stability of docetaxel. As such, Applicant concluded that the findings concerning the stabilization effects of an antioxidant for about 80 mg/mL docetaxel would be similar for docetaxel concentrations as low as about 40 mg/mL.

As shown in Examples 3-5, Applicant prepared injection concentrates comprising docetaxel, glycofurol, and α-lipoic acid. Applicant found that inclusion of α-lipoic acid at concentrations of about 1 mg/mL to about 20 mg/mL in injection concentrates comprising docetaxel and glycofurol stored at 40° C. for up to 1 month unexpectedly decreased the total peak area % of the unknown impurities compared to TAXOTERE®. Compare Example 2 with Examples 3-5. In particular, Applicant studied a formulation with docetaxel, glycofurol, and about 2 mg/mL, about 5 mg/mL, about 7.5 mg/mL or about 10 mg/mL α-lipoic acid, and found that after storage at 40° C. for up to 1 month, no unknown impurity was present in an amount greater than 0.2% (see Examples 3-5). Unknown impurities of greater than 0.2% require further characterization, as set forth by the International Conference on Harmonization of Technical Requirements for Registration of Pharmaceuticals for Humans ("ICH Guidelines").

Applicant also found that inclusion of α-lipoic acid at concentrations of about 5 mg/mL to about 20 mg/mL in injection concentrates comprising docetaxel and glycofurol stored at 40° C. for up to 3 months unexpectedly decreased the total peak area % of impurities compared to TAXOTERE® (i.e. less than about 2%). Compare Example 2 with Examples 4-5. Additionally, Applicant discovered that inclusion of α-lipoic acid at concentrations of about 5 mg/mL to about 20 mg/mL in injection concentrates comprising docetaxel and glycofurol stored at 40° C. for up to 3 months unexpectedly decreased the total peak area % of unknown impurities compared to TAXOTERE® (i.e. less than about 1%). Compare Example 2 with Examples 4-5. Surprisingly, Applicant further found that the inclusion of about 5 mg/mL α-lipoic acid reduced peak area % of individual unknown impurities to no more than 0.2% after storage at 40° C. for up to 3 months. See Example 4. Moreover, Applicant observed that α-lipoic acid at concentrations of about 1 mg/mL to about 20 mg/mL stabilized the formation of the known degradants, 10-oxo-docetaxel, 7-hydroxy-epi-docetaxel, and 7-epi-10-oxo-docetaxel. See Examples 3-5.

Applicant studied the formulation comprising docetaxel, glycofurol, and α-lipoic acid after initial dilution with a diluent, and observed that the initial diluted solution was clear and colorless after storage for up to 24 hours at room temperature. See Example 9. In addition, Applicant found that further dilution with an infusion solution for injection was clear and colorless after storage for up to 8 hours at room temperature. See Example 10.

Taken together, Applicant concluded that a formulation comprising docetaxel, glycofurol, and α-lipoic acid solubilized docetaxel, prevented its precipitation upon dilution, and avoided the use of polysorbates and polyethoxylated castor oil associated with side effects requiring patient premedication.

DEFINITIONS

As used herein, "docetaxel" refers to a drug substance having the chemical name of (2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate. Docetaxel has the following structural formula:

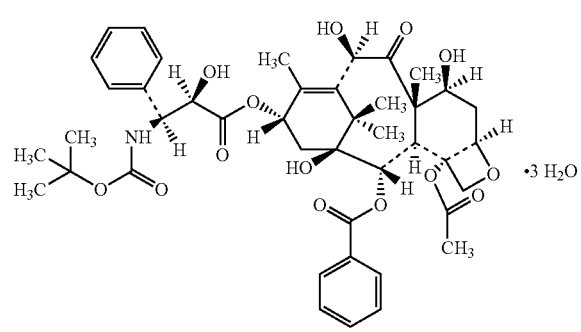

Docetaxel, as currently marketed by Sanofi-Aventis, is a white to almost-white powder with an empirical formula of $C_{43}H_{53}NO_{14}.3H_2O$, and a molecular weight, as a trihydrate, of 861.9.

As used herein, "injection concentrate" refers to a liquid solution comprising docetaxel dissolved in one or more excipients, wherein the solution requires an initial dilution and a final dilution in the infusion fluids prior to administration to a patient.

"Initial diluted solution" refers to the solution prepared by mixing the injection concentrate with a diluent.

"Final dilution for infusion" refers to the solution prepared by mixing the initial diluted solution with saline, water for injection, or the like.

As used herein, "solubilizer" refers to a solvent that is capable of dissolving docetaxel (or a pharmaceutically acceptable salt thereof) to prepare an injection concentrate. TWEEN 80®, glycofurol, benzyl alcohol and ethanol can be classified as solubilizers.

As used herein, "hydrotrope" refers to a material that can solubilize docetaxel or any such other lipophilic agent, if present in a sufficient quantity, and prevents the precipitation of docetaxel when the injection concentrate is further diluted to the initial diluted solution or final dilution for infusion. A hydrotrope does not dissolve the drug to the extent as the solubilizer. Two or more hydrotropes can act synergistically on solubility such that the combination can be used as a "solubilizer" in the context of the present invention. TPGS 1000, polyethylene glycol (PEG) 400, and propylene glycol (PG) are classified as hydrotropes, while 10% to 20% of ethanol can be used as a hydrotrope in combination with one or more hydrotropes.

As used herein, "substantially free" refers to the presence of a material in an amount less than about 5% (peak area %), or about 3%, or about 1%, or about 0.5%, or about 0.1%, or about 0% (i.e., totally free) as measured by HPLC with the UV detector set at a specific wavelength.

As used herein, "impurity" refers to any component of a drug product that is not the drug substance or an excipient in the drug product. See *ICH Guidelines: Impurities in New Drug Products* at 6. An impurity can include any degradant of a drug product.

As used herein, "unknown impurity" refers to an impurity of docetaxel other than 10-oxo-docetaxel, 7-hydroxy-epi-docetaxel, or 7-epi-10-oxo-docetaxel.

Formulation of a Docetaxel Injection Concentrate

The present invention relates to a formulation of a docetaxel injection concentrate comprising docetaxel or a pharmaceutically acceptable salt thereof, one or more solubilizers, and α-lipoic acid. The formulation is substantially free of excipients that can cause severe side effects and maintains chemical stability during storage.

Applicants have discovered that particular solubilizers may be used in formulations of docetaxel injection concentrate that do not induce severe side effects or do not likely require premedication with a steroid. If docetaxel is formulated without polyethoxylated castor oil or polysorbate 80, it should be better tolerated in cancer patients, thereby allowing these patients to take the medication for a longer period of time without dose interruption and/or reduction as compared to the current marketed formulation, i.e., TAXOTERE®. For example, docetaxel, formulated without polyethoxylated castor oil or polysorbate 80 can likely be administered to cancer patients at much higher doses than TAXOTERE®'s dosing range of 75 to 100 mg/m², at higher infusion rates (up to at least 1 mg/mL in 10 to 15 minutes infusion time), for longer exposure to the drug (more than six cycles), and/or with less than three weeks between cycles.

Additionally, if docetaxel can be formulated without polyethoxylated castor oil or polysorbate 80, it is likely it can be administered to cancer patients without premedicating with steroids. The reduction or elimination of the steroid pretreatment phase can reduce concerns of immune system depression and other side effects, as well as of interactions with other drugs that the patient may be taking. Also, eliminating polysorbates in the formulation can remove the risk of skin rashes, edema, hypotension and bradycardia.

The solubilizers of the present invention include, but are not limited to, acetic acid, benzyl alcohol, ethanol, and glycofurol. Glycofurol is also known as tetrahydrofurfuryl alcohol polyethylene glycol ether and has the following structure:

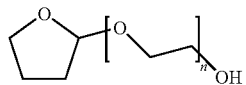

where n is on average 2, such as glycofurol 75, but may be other integers such as n=1.

Glycofurol may be combined with a liquid PEG, such as PEG 200 or PEG 400. The resulting mixture may comprise glycofurol and PEG in a ratio % of about 15:85 to about 85:15, or about 30:70 to about 70:30, or about 50:50.

Ethanol is another solubilizer that can be used in the injection concentrate, as docetaxel is highly soluble in ethanol (120 mg/mL).

The solubilizer may be present in the injection concentrate in an amount sufficient to bring the formulation to a final target volume, i.e., a quantity sufficient (q.s.) amount. For example, if the final target volume of the injection concentrate is about 1 mL, then the solubilizer may q.s. to about 1 mL.

As discussed in the Examples, Applicant surprisingly found that α-lipoic acid at particular concentrations, or pharmaceutically acceptable salts thereof, may be used in the formulation to stabilize docetaxel during storage. Unexpectedly, α-lipoic acid, or pharmaceutically acceptable salts thereof, in an amount of about 1 mg/mL to about 20 mg/mL may control the total peak area % of unknown impurities to less than about 0.75% as measured by HPLC after storage at 40° C. over 1 month. Also, α-lipoic acid, or a pharmaceutically acceptable salt thereof, in an amount of about 2 mg/mL, about 5 mg/mL, about 7.5 mg/mL or about 10 mg/mL, may maintain the peak area % of individual unknown impurities to levels no greater than 0.2% as measured by HPLC after storage at 40° C. over 1 month.

Also, α-lipoic acid, or pharmaceutically acceptable salts thereof, in an amount of about 1 mg/mL to about 20 mg/mL, may control the percent of initial concentration of docetaxel to no less than about 91% as measured by HPLC after storage at 40° C. for 3 months. Furthermore, α-lipoic acid, or pharmaceutically acceptable salts thereof, in an amount of about 5 mg/mL to about 20 mg/mL, may control the total peak area % of impurities to less than about 2% as measured by HPLC after storage at 40° C. over 3 months, and/or may maintain the total peak area % of unknown impurities to no greater than about 1% as measured by HPLC after storage at 40° C. over 3 months. Moreover, α-lipoic acid, or a pharmaceutically acceptable salt thereof, in an amount of about 5 mg/mL, may control the peak area % of individual unknown impurities to an amount no greater than 0.2%, as measured by HPLC after storage at 40° C. over 3 months.

Therefore, certain embodiments of the present invention may relate to injection concentrates comprising docetaxel, or a pharmaceutically acceptable salt thereof; and α-lipoic acid, or a pharmaceutically acceptable salt thereof, in an amount of about 1 to about 20 mg/mL, or about 1 to about 10 mg/mL, or about 5 to about 10 mg/mL, or about 5 mg/mL. The stability achieved by the injection concentrates may vary according to the concentration of α-lipoic acid that is present.

The stability provided by α-lipoic acid at lower concentrations (less than 5 mg/mL) may be enhanced by the presence of a low concentration of an acid, such as citric acid, or its salt. Thus, in certain embodiments, an injection concentrate may further comprise an acid, such as citric acid, or its salt, in an amount no greater than 10 mg/mL.

Docetaxel may be anhydrous or as a trihydrate, and may be present in the injection concentrate in an amount of about 20 to about 120 mg/mL, or about 40 to about 80 mg/mL. Stability as described above may be maintained in injection concentrates comprising docetaxel at concentrations other than about 80 mg/mL through particular concentrations of α-lipoic acid.

The docetaxel injection concentrate can be stored at room temperature (about 15 to about 30° C.) or under refrigerated conditions (about 2 to about 8° C.). The docetaxel injection concentrate can be stored for up to about two years, preferably from about one year to about one and half years, at room temperature and longer still under refrigeration.

The docetaxel injection concentrate may be lyophilized if formulated with ethanol for reconstitution to a concentrate material. The lyophilization procedure can follow methods of lyophilization known in the art.

The docetaxel injection concentrate may be substantially free of particular solubilizers such as polysorbates and polyethoxylated castor oil solubilizers. The polysorbates may include, but are not limited to TWEEN 20® and TWEEN 80®.

Formulation of a Docetaxel Initial Diluted Solution

The present invention also relates to the formulation of a docetaxel initial diluted solution comprising the docetaxel injection concentrate of the present invention and a diluent. The diluent solution may be used to dilute the injection concentrate to docetaxel concentrations of about 5 to about 20 mg/mL, or about 8 to about 15 mg/mL, or about 10 mg/mL. The resulting solution is the docetaxel initial diluted solution.

The diluent may comprise at least one hydrotrope and optionally a solubilizer, optionally a tonicity adjuster, and optionally a buffer or other pH modifier. The hydrotrope may include, but is not limited to, PEG such as PEG 400 and PEG 300; PG; 50% PEG 400/50% PG; LUTROL® (as known as SOLUTOL®) 2% in PEG; tocopherol compounds; and acetic acid. In certain embodiments, the hydrotrope may be TPGS, PEG, or a combination thereof. For example, the TPGS may be in an amount of about 100 mg/mL to about 250 mg/mL and PEG 400 in an amount of about 2.0 to about 3.5 mL per 7 mL of the diluent. The diluent may further comprise α-lipoic acid, and/or pharmaceutically acceptable salts thereof in a quantity such that the initial diluted solution comprises no more than about 200 mg/mL. Thus, the quantity of α-lipoic acid and/or pharmaceutically acceptable salts thereof in the diluent may depend on the quantity of α-lipoic acid, and/or pharmaceutically acceptable salts thereof in the injection concentrate.

The initial diluted solution may further comprise a tonicity adjuster. The tonicity adjuster may generally be a solute that alters the ionic concentration of the formulation without having a significant impact on the solubility and stability of docetaxel. In various embodiments the tonicity adjuster may be selected from inorganic salts, organic salts, sugars or combinations thereof. Examples of inorganic salts include sodium chloride, potassium chloride, and magnesium chloride. Organic salts may include but are not limited to sodium acetate and sodium citrate. Sugars that are contemplated to be tonicity adjusters within the scope of the present invention may include dextrose, mannitol, sucrose, and the like. In certain embodiments the tonicity adjuster may be sodium chloride in a concentration of about 1 mg/mL to about 25 mg/mL, or about 2.5 mg/mL to about 20 mg/mL, or about 5 mg/mL to about 15 mg/mL, or about 8 mg/mL to about 10 mg/mL.

The initial diluted solution may further comprise a pH-adjusting agent such as a base or a buffer. The bases may be one or more inorganic bases or organic bases, including, but not limited to, alkaline carbonate, alkaline bicarbonate, alkaline earth metal carbonate, alkaline hydroxide, alkaline earth metal hydroxide or amine. For example, the inorganic or organic base may be an alkaline hydroxide such as lithium hydroxide, potassium hydroxide, cesium hydroxide, sodium hydroxide or the like; an alkaline carbonate such as calcium carbonate, sodium carbonate or the like; or an alkaline bicarbonate such as sodium bicarbonate or the like; the organic base may also be sodium acetate. The buffer may comprise organic buffer materials that include, without limitation, the following materials together with their conjugate salts (which free compound/salt conjugate may form in situ from either the free compound or the conjugate salt being added alone as known in the art of buffer materials): hydroxyl acids such as citric acid and lactic acid, etc; dicarboxylic acids such as adipic acid and succinic acid, etc; and amino acids such as, without limitation, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, etc. The buffer may also be phosphate buffer or carbonate/bicarbonate buffer. The pH-adjusting agent may be used to modify the pH of the initial diluted solution to between about 6 and about 8, or between about 6.5 and about 7.0.

The initial diluted solution may be substantially free of polysorbate 80, CREMOPHOR®, and/or all polyethoxylated vegetable oils (whether totally hydrogenated, partially hydrogenated, or not hydrogenated). In addition, the initial diluted solution may be substantially free of ethanol and/or hydroxyalkyl substituted cellulosic polymers.

Furthermore, the initial diluted solution may comprise various volumes according to its use. For example, to prepare the final dilution for infusion, the initial diluted solution may comprise a volume of about 2 mL to about 20 mL, or about 5 mL to about 12 mL, or about 8 mL.

The initial diluted solution can be stored at about room temperature for at least about 24 hours, as these conditions will generate no detectable levels of impurities. In addition, after storage at room temperature for up to 24 hours, the initial diluted solution will be clear and colorless. Moreover, the potency of the docetaxel in the initial diluted solution may remain at 100%. The initial diluted solution can also be stored under refrigerated conditions (about 2 to about 8° C.) for even longer periods of time.

Formulation of a Docetaxel Final Dilution for Infusion

The present invention also relates to the formulation of a docetaxel final dilution for infusion comprising the initial diluted solution mixed with an infusion solution such as water for injection, 0.9% sodium chloride solution (or normal saline), 50% dextrose solution, or the like. The final dilution for infusion may be appropriate for injection into patients.

The final dilution for infusion may comprise docetaxel having a concentration of about 0.32 mg/mL to about 0.74 mg/mL. Therefore, the initial diluted solution will be added to the appropriate amount of the infusion solution, which may be dependent on the concentration of docetaxel in the initial diluted solution. For example, if the initial diluted solution contains 10 mg/mL of docetaxel, preparation of the final dilution for infusion would involve mixing 1 mL of the initial diluted solution with infusion solution of about 30.25 mL or about 12.51 mL to result in a final dilution for infusion having a docetaxel concentration of about 0.32 mg/mL or about 0.74 mg/mL, respectively.

The final dilution for infusion can be stored at room temperature for at least about 8 hours, as these conditions generate no detectable levels of impurities. In addition, after storage at room temperature for up to 8 hours, the final dilution for infusion will be clear and colorless. Moreover, the potency of the docetaxel in the final dilution for infusion will remain at 100 or 99%.

Packages and Kits

The present invention also relates to a package/kit comprising the injection concentrate and the diluent of the invention. The injection concentrate and the diluent may be housed in separate vessels that include vials or containers.

The package/kit may comprise a withdrawing means such as a syringe, and/or a means to alter the temperature of the vials, e.g., modify the temperature of the vials to room temperature. The package/kit may also contain instructions for diluting the injection concentrate using the diluent.

Single-Vial and Multi-Dose Vial Docetaxel Presentations

A docetaxel injection concentrate of the instant invention that avoids the use of polyethoxylated castor oil and polysorbates, and which is stable for extended periods of time, offers significant advantages over TAXOTERE®. Applicant recognizes that yet a further benefit to the medical community is single-vial and multi-dose vial docetaxel presentations having all of the same advantages but that do not require dilution prior to addition to the infusion solution. Such a presentation decreases the handling of the drug product prior to administration, thereby minimizing dilution error and loss of active agent due to manipulation. Moreover, such a drug product would need to have a reasonable shelf-life for it to be commercially viable. To this end, single-vial and multi-dose vial presentations of docetaxel of the instant invention are prepared that will comprise at least one solubilizer, at least one stabilizer, and at least one hydrotrope; such presentations may further include optionally a tonicity adjuster, and optionally an acid buffer or other pH modifier.

Single-vial and multi-dose vial formulations contemplated by Applicant comprise docetaxel in concentrations of about 5 mg/mL to about 20 mg/mL, or about 8 mg/mL to about 15 mg/mL, or about 10 mg/mL. The solubilizer may include, but is not limited to, acetic acid, benzyl alcohol, ethanol, and glycofurol. The solubilizer may be glycofurol in a total amount of about 1 mL to about 2 mL. Alternatively, glycofurol may be combined with a PEG, such as PEG 300 or PEG 400 to solubilize docetaxel. The total volume of PEG in the single-vial and multi-dose vial formulations may be about 1 mL to about 10 mL, or about 2 mL to about 7 mL, or about 3 mL to about 6 mL. The stabilizer contemplated by the instant invention may comprise α-lipoic acid, or pharmaceutically acceptable salts thereof, present in an amount of about 5 mg/mL to about 100 mg/mL, or present in an amount of about 5 mg/mL to about 25 mg/mL, or present in an amount of about 10 mg/mL to about 20 mg/mL. The hydrotrope may include, but is not limited to, PEG such as PEG 300 and PEG 400, PG, 50% PEG 400/50% PG, LUTROL® 2% in PEG; tocopherol compounds, and acetic acid. In certain embodiments, the hydrotrope may be TPGS 1000, PEG, or a combination thereof. For example, the TPGS may be in an amount of about 1 g to about 2 g, or about 1.5 g.

In some embodiments wherein the concentration of α-lipoic acid is low, i.e., less than 5 mg/mL, an acid, such as a citric acid, or its salt may be added to further stabilize the injection concentrate. Hence, the acid buffer may be present in the formulation in a concentration of less than 10 mg/mL.

The single-vial and multi-dose vial presentations of docetaxel of the instant invention also may comprise optionally a tonicity adjuster and optionally a buffer or other pH modifier. The tonicity adjuster may generally be a solute that alters the ionic concentration of the formulation without having a significant impact on the solubility and stability of docetaxel. In various embodiments the tonicity adjuster may be selected from inorganic salts, organic salts, sugars or combinations thereof. Examples of inorganic salts include sodium chloride, potassium chloride, and magnesium chloride. Organic salts may include but are not limited to sodium acetate and sodium citrate. Sugars that are contemplated to be tonicity adjusters within the scope of the present invention may include dextrose, mannitol, sucrose, and the like. In certain embodiments the tonicity adjuster may be sodium chloride in a concentration of about 1 mg/mL to about 25 mg/mL, or about 2.5 mg/mL to about 20 mg/mL, or about 5 mg/mL to about 15 mg/mL, or about 8 mg/mL to about 10 mg/mL.

The buffer of the docetaxel single-vial and multi-dose vial presentations may be generally in an amount of about 0.5 mg to about 2 mg of phosphate or citrate buffer for about each mg of α-lipoic acid, and/or pharmaceutically acceptable salts thereof. The buffer may be selected so as to be capable of buffering the formulation to a pH of about 5 to about 7.5, or about 6 to about 7. Appropriate amounts of the free acid or base used and its conjugate salt to create the buffer will be within the ability of those of ordinary skill in the art. Alternate organic buffer materials may include, without limitation, the following materials together with their conjugate salts (which free compound/salt conjugate may form in situ from either the free compound or the conjugate salt being added alone as known in the art of buffer materials): hydroxyl acids such as citric acid and lactic acid, etc; dicarboxylic acids such as adipic acid and succinic acid, etc; and amino acids such as, without limitation, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, etc. Potassium hydroxide or sodium hydroxide can be used to increase the pH of the single-vial or multi-dose vial formulation to a target range of about 5 to about 7.5. Hydrochloric acid or additional phosphoric acid can be used as needed to decrease the pH to the target range. Bicarbonate or carbonate salts, especially sodium or potassium salts thereof, may be used to adjust pH as well.

Examples of docetaxel single-vial presentations or multi-dose-vial presentations and the stability conditions under which they are evaluated are shown in Example 11.

Methods of Preparing Docetaxel for Administration to a Patient in Need Thereof

The present invention relates to a method of preparing an injection concentrate. The method may comprise mixing one or more solubilizers, α-lipoic acid and docetaxel to form the injection concentrate. The volume of the injection concentrate may then be adjusted by adding more of the solubilizer(s). The solubilizers of the present invention may include, but are not limited to, acetic acid, benzyl alcohol, ethanol, and, glycofurol, as described above.

The addition of one or more solubilizers, α-lipoic acid and docetaxel can be achieved by methods known in the art. For example, one or more solubilizers, α-lipoic acid and docetaxel may be added to each other and then mixed in a common receptacle, or a combination thereof. In one embodiment, the one or more solubilizers, α-lipoic acid and docetaxel may be added all together. In another embodiment, the one or more solubilizers, α-lipoic acid and docetaxel may be added simultaneously. In yet another embodiment, the one or more solubilizers, α-lipoic acid and docetaxel may be added individually in a particular order or individually in any order. The one or more solubilizers, α-lipoic acid and docetaxel also may be added in any combination herein.

The one or more solubilizers, α-lipoic acid and docetaxel may be mixed by methods known in the art. For example, one or more solubilizers, α-lipoic acid and docetaxel can be mixed by simple mixing. In another embodiment, the one or more solubilizers, α-lipoic acid and docetaxel may be mixed with a mixing device continuously, periodically, or a combination thereof. Mixing devices may include, but are not limited to, a magnetic stirrer, shaker, a paddle mixer, homogenizer, and any combination thereof.

The addition and mixing of one or more solubilizers, α-lipoic acid and docetaxel may occur under controlled conditions. For example, the addition and mixing of one or more solubilizers, α-lipoic acid and docetaxel may occur under conditions such as under nitrogen or at a particular humidity, etc. Additionally, light exposure can be controlled during the addition and mixing of one or more solubilizers, α-lipoic acid and docetaxel using methods known in the art. For example, manufacturing can be carried out in yellow light or the batch vessel can be protected from direct exposure to light.

After the injection concentrate is prepared, it may be sterilized by methods known in the art. The injection concentrate may undergo aseptic filtration (e.g., using a 0.2 μm disposable membrane filter). In another embodiment, the injection concentrate may undergo a freeze-thaw cycle to kill any residual vegetative bacteria.

Additionally, the injection concentrate may be placed into a container (e.g. an intravenous solution bag, bottle, vial, ampoule, or pre-filled sterile syringe). The container may have a sterile access port for piercing by a hypodermic injection needle.

A summary of the steps for preparing an injection concentrate according to an embodiment of the invention is shown in FIG. 1.

Figure 2:
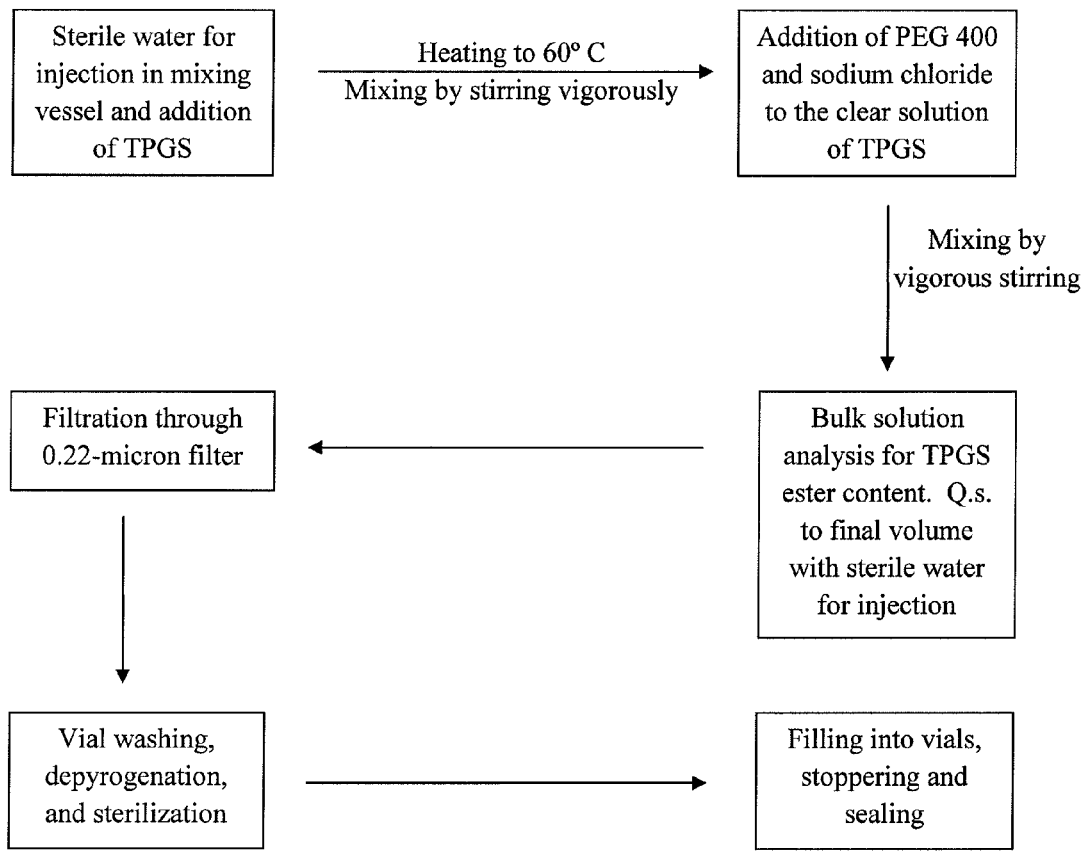
FIG. 2 is a flow diagram showing steps for preparing a diluent according to an embodiment of the invention.

The injection concentrate may then be mixed with a diluent to form an initial diluted solution. As described above, the diluent may comprise at least one hydrotrope and optionally a solubilizer, optionally a tonicity adjuster, and optionally an acid buffer or other pH modifier, as described as above. A summary of the steps for preparing a diluent according to an embodiment of the invention is shown in FIG. 2.

The initial diluted solution may be formed by mixing the injection concentrate and diluent together. In one embodiment the injection concentrate may be added to the diluent. In another embodiment, the diluent may be added to the injection concentrate. In yet another embodiment, the injection concentrate and diluent may be combined together in a pre-sterilized vessel. The injection concentrate and diluent may be mixed by repeated inversions, swirling, or other techniques known in the art. Due the absence of polysorbates in the diluent and the injection concentrate, little to no foaming occurs during the mixing.

In another embodiment, the preparation of a single concentrate for final dilution for infusion can be achieved by combining all the ingredients in the injection concentrate and the diluent. For example, one or more solubilizers, α-lipoic acid, docetaxel, at least one hydrotrope and optionally a tonicity adjuster, and optionally an acid buffer or other pH modifier can be combined through mixing to form the initial diluted solution. The addition of these components can be achieved by methods known in the art. For example, one or more solubilizers, α-lipoic acid, docetaxel, at least one hydrotrope and optionally a tonicity adjuster, and optionally an acid buffer or other pH modifier may be added to each other and then mixed in a common receptacle, or a combination thereof. In another embodiment, these components may be added individually in a particular order or individually in any order. In yet another embodiment, these components may be added simultaneously. The addition of these components may also be achieved by a combination of methods describes herein.

The one or more solubilizers, α-lipoic acid, docetaxel, at least one hydrotrope and optionally a tonicity adjuster, and optionally a buffer or other pH modifier may be mixed by methods known in the art. For example, the components may be mixed by simple mixing. The components may also be mixed constantly, sporadically, or a combination thereof using a mixing device. The components may be mixed using, for example, a paddle mixer, magnetic stirrer, shaker, homogenizer, and any combination thereof.

Preparing the initial diluted solution may occur under controlled conditions. For example, the dilution of the injection concentrate may occur under conditions such as under nitrogen or at a particular humidity, etc. Additionally, light exposure can be controlled during the dilution of the injection concentrate by using methods known in the art.

After the initial diluted solution is prepared, it may be sterilized by methods known in the art. The injection concentrate may undergo aseptic filtration (e.g. using a 0.2 μm disposable membrane filter). In another embodiment, the injection concentrate may undergo a freeze-thaw cycle to kill any residual vegetative bacteria.

The initial diluted solution may then undergo final dilution with an infusion solution. The infusion solution may include, but is not limited to, normal saline, 5% dextrose, water for injection, or other suitable injection diluents for administration to the patient, to form a final dilution for infusion.

As the present invention is directed to delivery of docetaxel, once diluted to appropriate injection (especially infusion, most particularly IV infusion) concentrations, it may be administered in appropriate amounts for treating docetaxel responsive conditions known in the art. In addition, the present invention permits administration of higher doses and concentrations of docetaxel than the currently marketed TAXOTERE®. As such, the concentrates and administrable dosage forms thereof made from the present invention are also useful to treat docetaxel-responsive indications known in the art for which the current marketed TAXOTERE® formulation is not recommended because of an inability to administer docetaxel at a sufficiently high dose, either acutely or cumulatively. These include, without limitation, carcinomas such as colorectal, prostate, pancreatic, renal, and liquid tumors like lymphoma and leukemia.

Administration of the docetaxel final dilution for infusion to the patient may not require premedication with a steroid. Antihistamines are likely not required as a pretreatment but may be administered to the patient as a precaution.

The invention will now be further described by way of the following non-limiting examples, which further illustrate the invention; such examples are not intended, nor should they be interpreted, to limit the scope of the invention.

EXAMPLES

Example 1

In consideration of the severe side effects associated with the use of polysorbates, such as TWEEN 80®, as solubilizers of docetaxel, solubility studies were conducted to determine non-toxic solvents that can effectively dissolve docetaxel.

Solubility of docetaxel was assessed using several different solvents that are well-tolerated in subjects, as well as polysorbates for comparison. The solubility data for these solvents are summarized in Table 1.

TABLE 1

Solubility of Docetaxel in Various Solvents

| Solvents | Concentration (mg/mL) |
| --- | --- |
| TWEEN 80 ®* | 60 |
| TWEEN 20 ®* | 90 |
| PEG 400 | 10 |
| Propylene Glycol | 10 |
| 50% PEG 400/50% PG | 15 |
| 2% Lutrol in PEG 400 | 15 |
| Glycerol | 1.65 |
| Span 80 | 3.5 |
| TPGS 1000 | 50 |
| LABROFAC ™ (Capric triglyceride PEG 4 ester Macrogol 200) | 35 |

TABLE 1-continued

Solubility of Docetaxel in Various Solvents

| Solvents | Concentration (mg/mL) |
|---|---|
| PECEOL ® (Glycerol mono Oleate 40) | 7 |
| MAISINE ™ 35-1 (Glycerol mono linoleate) | 10 |
| Ethanol | 120 |
| N-Methyl 2-Pyrrolidone | 17.6 |
| Benzyl alcohol | 90 |
| Benzyl benzoate | 13 |
| Acetic acid | 60 |
| 1-lactic acid | 6 |
| Glycofurol | 200 |

*polysorbates were included for comparison

The results indicate that TPGS 1000, benzyl alcohol, acetic acid, ethanol and glycofurol were comparable or superior to TWEEN 80® and TWEEN 20® with respect to solubilizing docetaxel. Docetaxel was most soluble in glycofurol.

Example 2

The stability of an injection concentrate comprising docetaxel dissolved in glycofurol was compared to the brand product, TAXOTERE®, which comprises docetaxel dissolved in TWEEN 80®.

Stability was determined using high performance liquid chromatography (HPLC) under the conditions described in Table 2.

TABLE 2

HPLC Equipment, Standards and Solvents, and Method

| Equipment | |
|---|---|
| Chromatographic System | Waters 2695 Separations Module with 2995 Detector with Empower2 Software |
| Electronic Balance | Mettler, Model No. XS105 (0.01 mg sensitivity) |
| Laboratory Glassware | Class-A Volumetric Flasks and Pipettes |
| Standards and Solvents | |
| Docetaxel Standard | Standardized known purity of Docetaxel |
| Acetonitrile | HPLC Grade (Rankem) |
| Methanol | HPLC Grade (Rankem) |
| Water | Milli - Q (Millipore) |
| Sodium Hydroxide | AR grade (Rankem) |
| Hydrochloric Acid | GR grade (Rankem) |
| Hydrogen Peroxide | AR grade (Rankem) |
| Method | |
| Colunm | Zorbax SB - $C_{18}$, 250 mm × 4.6 mm 5µm particle size |
| Mobile Phase | Water: ACN: Methanol (32:42:26) |
| Flow Rate | 1.0 mL/min |
| Detection Wavelength | 230 nm |
| Column Temperature | Ambient |
| Injection Volume | 10 µL |
| Run Time | 20 min |
| Diluent | Mobile Phase |

Three major degradation products were identified using this HPLC method: 10-oxo-docetaxel ("10-oxo-DCT"), which refers to a docetaxel degradant comprising an oxo formation at the C10 position; 7-hydroxy-epi-docetaxel ("7-epi-DCT"), which refers to a docetaxel degradant comprising epimerization at the C7 position; and 7-epi-10-oxo-docetaxel ("7-epi-10-oxo-DCT"), which refers to a docetaxel degradant comprising both epimerization at the C7 position followed by an oxo formation at the C10 position. See generally, Kumar et al., J. Pharm. Biomed. Anal., 43 (2007) 1228-35. The relative retention time ("RRT") associated with each of these degradants is shown in Table 3.

TABLE 3

RRT for the Known Degradants of Docetaxel

| Docetaxel Degradant | RRT |
|---|---|
| 10-oxo-DCT | 1.16-1.19 |
| 7-epi-DCT | 1.43-1.48 |
| 7-epi-10-oxo-DCT | 1.58-1.65 |

In the stability studies, injection concentrates comprising docetaxel dissolved in glycofurol were prepared. The docetaxel concentration was either 80 mg/mL or 40 mg/mL. The injection concentrates were stored at 40° C. over 1, 2, or 3 months, or were stored at 25° C. over 3, 6, or 9 months, or 1 or 2 years. The stability results are outlined in Table 4 (80 mg/mL docetaxel) and Table 5 (40 mg/mL docetaxel).

TABLE 4

Stability of Injection Concentrate Comprising Docetaxel (80 mg/mL) and Glycofurol

| Storage Temp. | Time period | % of Initial | Impurity | Peak Area % of Impurities |
|---|---|---|---|---|
| | Initial | 100 | 7-epi-DCT | 0.07 |
| 40° C. | 1 month | 99 | Unknown (RRT 0.21) | 0.11 |
| | | | Unknown (RRT 0.39) | 0.12 |
| | | | Unknown (RRT 0.48) | 0.05 |
| | | | 10-oxo-DCT | 0.36 |
| | | | 7-epi-DCT | 0.12 |
| | | | | Total: 0.76 |
| | 2 months | 98 | Unknown (RRT 0.19) | 0.20 |
| | | | Unknown (RRT 0.29) | 0.05 |
| | | | Unknown (RRT 0.38) | 0.22 |
| | | | Unknown (RRT 0.46) | 0.09 |
| | | | Unknown (RRT 0.87) | 0.05 |
| | | | Unknown (RRT 1.64) | 0.09 |
| | | | 10-oxo-DCT | 0.45 |
| | | | 7-epi-DCT | 0.16 |
| | | | | Total: 1.31 |
| | 3 months | 99 | Unknown (RRT 0.20) | 0.28 |
| | | | Unknown (RRT 0.35) | 0.12 |
| | | | Unknown (RRT 0.40) | 0.21 |
| | | | Unknown (RRT 0.46) | 0.05 |
| | | | Unknown (RRT 0.48) | 0.25 |
| | | | Unknown (RRT 0.52) | 0.05 |
| | | | 10-oxo-DCT | 0.82 |
| | | | 7-epi-DCT | 0.26 |
| | | | 7-epi-10-oxo-DCT | 0.28 |
| | | | | Total: 2.32 |
| 25° C. | 3 months | 99 | Unknown (RRT 0.88) | 0.05 |
| | | | 10-oxo-DCT | 0.28 |
| | | | 7-epi-DCT | 0.09 |
| | | | | Total: 0.42 |
| | 6 months | 97 | Unknown (RRT 0.24) | 0.12 |
| | | | Unknown (RRT 0.40) | 0.18 |
| | | | 10-oxo-DCT | 0.47 |
| | | | 7-epi-DCT | 0.27 |
| | | | 7-epi-10-oxo-DCT | 0.33 |
| | | | | Total: 1.37 |
| | 1 year | 95 | Unknown (RRT 0.38) | 0.11 |
| | | | Unknown (RRT 0.46) | 0.12 |
| | | | 10-oxo-DCT | 1.06 |
| | | | 7-epi-DCT | 0.41 |
| | | | 7-epi-10-oxo-DCT | 1.26 |
| | | | | Total: 2.96 |
| | 2 year | 90 | Unknown (RRT 0.19) | 0.20 |
| | | | Unknown (RRT 0.33) | 0.33 |
| | | | Unknown (RRT 0.39) | 0.26 |
| | | | Unknown (RRT 0.45) | 0.31 |
| | | | Unknown (RRT 0.63) | 0.59 |

TABLE 4-continued

Stability of Injection Concentrate
Comprising Docetaxel (80 mg/mL) and Glycofurol

| Storage Temp. | Time period | % of Initial | Impurity | Peak Area % of Impurities |
|---|---|---|---|---|
| | | | Unknown (RRT 0.75) | 0.09 |
| | | | Unknown (RRT 0.95) | 0.10 |
| | | | Unknown (RRT 1.99) | 0.09 |
| | | | 10-oxo-DCT | 1.36 |
| | | | 7-epi-DCT | 0.51 |
| | | | 7-epi-10-oxo-DCT | 1.92 |
| | | | | Total: 5.76 |

TABLE 5

Stability of Injection Concentrate
Comprising Docetaxel (40 mg/mL) and Glycofurol

| Storage Temp. | Time period | % of Initial | Impurity | Peak Area % of Impurities |
|---|---|---|---|---|
| | Initial | 100 | 7-epi-DCT | 0.07 |
| 40° C. | 1 month | 99 | Unknown (RRT 0.21) | 0.12 |
| | | | Unknown (RRT 0.40) | 0.12 |
| | | | Unknown (RRT 0.48) | 0.05 |
| | | | 10-oxo-DCT | 0.42 |
| | | | 7-epi-DCT | 0.13 |
| | | | | Total: 0.84 |
| | 2 months | 96 | Unknown (RRT 0.20) | 0.30 |
| | | | Unknown (RRT 0.31) | 0.09 |
| | | | Unknown (RRT 0.40) | 0.25 |
| | | | Unknown (RRT 0.48) | 0.11 |
| | | | 10-oxo-DCT | 0.48 |
| | | | 7-epi-DCT | 0.15 |
| | | | 7-epi-10-oxo-DCT | 0.05 |
| | | | | Total: 1.43 |
| | 3 months | 93 | Unknown (RRT 0.20) | 0.36 |
| | | | Unknown (RRT 0.35) | 0.25 |
| | | | Unknown (RRT 0.40) | 0.19 |
| | | | Unknown (RRT 0.46) | 0.10 |
| | | | Unknown (RRT 0.48) | 0.34 |
| | | | Unknown (RRT 0.51) | 0.07 |
| | | | 10-oxo-DCT | 1.00 |
| | | | 7-epi-DCT | 0.24 |
| | | | 7-epi-10-oxo-DCT | 0.26 |
| | | | | Total: 2.81 |
| 25° C. | 3 months | 99 | Unknown (RRT 0.20) | 0.07 |
| | | | Unknown (RRT 0.87) | 0.05 |
| | | | 10-oxo-DCT | 0.24 |
| | | | 7-epi-DCT | 0.09 |
| | | | | Total: 0.45 |
| | 6 months | 97 | Unknown (RRT 0.24) | 0.13 |
| | | | Unknown (RRT 0.40) | 0.17 |
| | | | 10-oxo-DCT | 0.54 |
| | | | 7-epi-DCT | 0.25 |
| | | | 7-epi-10-oxo-DCT | 0.39 |
| | | | | Total: 1.48 |
| | 1 year | 90 | Unknown (RRT 0.37) | 0.31 |
| | | | Unknown (RRT 0.46) | 0.11 |
| | | | 10-oxo-DCT | 1.42 |
| | | | 7-epi-DCT | 0.70 |
| | | | 7-epi-10-oxo-DCT | 2.11 |
| | | | | Total: 4.65 |
| | 2 years | 83 | Unknown (RRT 0.20) | 0.17 |
| | | | Unknown (RRT 0.44) | 0.15 |
| | | | Unknown (RRT 0.46) | 0.18 |
| | | | Unknown (RRT 0.63) | 1.36 |
| | | | Unknown (RRT 0.75) | 0.33 |
| | | | Unknown (RRT 0.95) | 0.11 |
| | | | Unknown (RRT 1.99) | 0.10 |
| | | | 10-oxo-DCT | 2.24 |
| | | | 7-epi-DCT | 0.82 |
| | | | 7-epi-10-oxo-DCT | 3.63 |
| | | | | Total: 9.09 |

Both injection concentrates have similar impurity profiles at 40° C. up to 3 months, indicating that the drug-to-solvent ratio did not adversely affect the solution stability of docetaxel.

TAXOTERE®, which comprises docetaxel (40 mg/mL) dissolved in TWEEN 80®, was obtained and stored at 40° C. over 1, 2, or 3 months. The stability results as determined by HPLC are outlined in Table 6.

TABLE 6

Stability of TAXOTERE® Comprising Docetaxel
(40 mg/mL) and TWEEN 80®

| Storage Temp. | Time period | % of Initial | Impurity | Peak Area % of Impurities |
|---|---|---|---|---|
| | Initial | 100 | Unknown (RRT 0.20) | 0.10 |
| | | | Unknown (RRT 0.35) | 0.05 |
| | | | Unknown (RRT 0.94) | 0.16 |
| | | | 10-oxo-DCT | 0.11 |
| | | | 7-epi-DCT | 0.04 |
| | | | | Total: 0.46 |
| 40° C. | 1 month | 99 | Unknown (RRT 0.20) | 0.13 |
| | | | Unknown (RRT 0.33) | 0.28 |
| | | | Unknown (RRT 0.37) | 0.11 |
| | | | Unknown (RRT 0.84) | 0.09 |
| | | | Unknown (RRT 0.95) | 0.14 |
| | | | 10-oxo-DCT | 0.13 |
| | | | 7-epi-DCT | 0.08 |
| | | | | Total: 9.96 |
| | 2 months | 97 | Unknown (RRT 0.22) | 0.17 |
| | | | Unknown (RRT 0.33) | 0.24 |
| | | | Unknown (RRT 0.36) | 0.09 |
| | | | Unknown (RRT 0.59) | 0.04 |
| | | | Unknown (RRT 0.84) | 0.15 |
| | | | Unknown (RRT 0.95) | 0.15 |
| | | | 10-oxo-DCT | 0.12 |
| | | | 7-epi-DCT | 0.08 |
| | | | | Total: 1.04 |
| | 3 months | 94 | Unknown (RRT 0.21) | 0.09 |
| | | | Unknown (RRT 0.33) | 0.14 |
| | | | Unknown (RRT 0.60) | 0.06 |
| | | | Unknown (RRT 0.84) | 0.51 |
| | | | Unknown (RRT 0.95) | 0.21 |
| | | | Unknown (RRT 2.25) | 0.14 |
| | | | 10-oxo-DCT | 0.20 |
| | | | 7-epi-DCT | 0.53 |
| | | | 7-epi-10-oxo-DCT | 0.10 |
| | | | | Total: 1.98 |

When comparing the stability of the injection concentrates to TAXOTERE® after storage at 40° C. after 3 months, TAXOTERE® experienced a loss of potency of about 6%. This loss was only slightly less than the injection concentrate comprising 40 mg/mL of docetaxel, but was greater than the injection concentrate comprising 80 mg/mL, over the same storage conditions.

Some unknown impurities generated in TAXOTERE® were not generated in the injection concentrate formulations, such as the impurities associated with RRT 0.59 and 0.84. Regardless, the total peak area % of all impurities in the docetaxel 40 mg/mL and 80 mg/mL formulations were comparable to that of TAXOTERE® (less than about 1%) at 40° C. for 1 month (0.76 and 0.84 versus 0.96, respectively). Yet, the total peak area % of all impurities of TAXOTERE® was less after storage at 40° C. for 2 and 3 months as compared to the total peak area % of all impurities of either injection concentrate formulations. This was primarily due to the generation of the known degradants 10-oxo-DCT, 7-epi-DCT, and 7-epi-10-oxo-DCT, which were higher in both injection concentrates.

Example 3

To decrease the production of known degradants 10-oxo-DCT, 7-epi-DCT, and 7-epi-10-oxo-DCT and improve stability of the injection concentrates, the effects of adding an antioxidant to the formulations were studied.

Injection concentrates comprising docetaxel (80 mg/mL), glycofurol (q.s. to 1 mL), and the antioxidant, α-lipoic acid, at concentrations of 0.5, 1, or 2 mg/mL were prepared. The injection concentrates were stored at 40° C. for up to 6 months, or 25° C. for up to 1 year, and their stability was assessed using the HPLC method described in Example 2. The results are outlined in Tables 7 (α-lipoic acid at 0.5 mg/mL), 8 (α-lipoic acid at 1 mg/mL), and 9 (α-lipoic acid at 2 mg/mL).

TABLE 7

Stability of Injection Concentrate Comprising Docetaxel (80 mg/mL), Glycofurol (q.s. to 1 mL), and α-lipoic acid (0.5 mg/mL)

| Storage Temp. | Time period | % of Initial | Impurity | Peak Area % Of Impurities |
|---|---|---|---|---|
| Initial | | 100 | 7-epi-DCT | 0.07 |
| 40° C. | 1 month | 96 | Unknown (RRT 0.64) | 0.85 |
| | | | Unknown (RRT 0.76) | 0.23 |
| | | | Unknown (RRT 0.80) | 0.27 |
| | | | Unknown (RRT 0.88) | 0.06 |
| | | | 10-oxo-DCT | 0.28 |
| | | | 7-epi-DCT | 0.26 |
| | | | | Total: 1.95 |
| | 2 months | | N/A (due to technical reasons) | |
| | 3 months | 89 | Unknown (RRT 0.24) | 0.06 |
| | | | Unknown (RRT 0.47) | 0.13 |
| | | | Unknown (RRT 0.63) | 2.89 |
| | | | Unknown (RRT 0.70) | 0.05 |
| | | | Unknown (RRT 0.75) | 1.48 |
| | | | Unknown (RRT 0.78) | 0.56 |
| | | | Unknown (RRT 0.89) | 0.18 |
| | | | 10-oxo-DCT | 0.46 |
| | | | 7-epi-DCT | 0.35 |
| | | | | Total: 6.16 |
| 25° C. | 3 months | 98 | Unknown (RRT 0.64) | 0.76 |
| | | | Unknown (RRT 0.76) | 0.12 |
| | | | Unknown (RRT 0.80) | 0.17 |
| | | | Unknown (RRT 0.87) | 0.05 |
| | | | 10-oxo-DCT | 0.26 |
| | | | 7-epi-DCT | 0.12 |
| | | | | Total: 1.48 |

TABLE 8

Stability of Injection Concentrate Comprising Docetaxel (80 mg/mL), Glycofurol (q.s. to 1 mL), and α-lipoic acid (1 mg/mL)

| Storage Temp. | Time period | % of Initial | Impurity | Peak Area % of Impurities |
|---|---|---|---|---|
| | Initial | 100 | 7-epi-DCT | 0.07 |
| 40° C. | 1 month | 99 | Unknown (RRT 0.64) | 0.14 |
| | | | Unknown (RRT 0.87) | 0.05 |
| | | | 10-oxo-DCT | 0.20 |
| | | | 7-epi-DCT | 0.28 |
| | | | 7-epi-10-oxo-DCT | 0.06 |
| | | | | Total: 0.73 |
| | 2 months | 97 | Unknown (RRT 0.64) | 1.66 |
| | | | Unknown (RRT 0.75) | 0.45 |
| | | | Unknown (RRT 0.79) | 0.20 |
| | | | 10-oxo-DCT | 0.30 |
| | | | 7-epi-DCT | 0.20 |
| | | | | Total: 2.81 |
| | 3 months | 91 | Unknown (RRT 0.19) | 0.25 |
| | | | Unknown (RRT 0.23) | 0.05 |
| | | | Unknown (RRT 0.63) | 3.73 |
| | | | Unknown (RRT 0.75) | 2.44 |
| | | | Unknown (RRT 0.78) | 0.84 |
| | | | Unknown (RRT 0.89) | 0.34 |
| | | | 10-oxo-DCT | 0.49 |
| | | | 7-epi-DCT | 0.30 |
| | | | | Total: 8.44 |
| | 6 months | 82 | Unknown (RRT 0.20) | 0.17 |
| | | | Unknown (RRT 0.63) | 2.59 |
| | | | Unknown (RRT 0.75) | 3.04 |
| | | | Unknown (RRT 0.88) | 0.19 |
| | | | 10-oxo-DCT | 0.58 |
| | | | 7-epi-DCT | 0.25 |
| | | | | Total: 6.82 |
| 25° C. | 3 months | 98 | Unknown (RRT 0.87) | 0.09 |
| | | | 10-oxo-DCT | 0.18 |
| | | | 7-epi-DCT | 0.25 |
| | | | 7-epi-10-oxo-DCT | 0.07 |
| | | | | Total: 0.59 |
| | 6 months | 93 | Unknown (RRT 0.63) | 0.30 |
| | | | Unknown (RRT 0.73) | 0.16 |
| | | | 10-oxo-DCT | 0.21 |
| | | | 7-epi-DCT | 0.15 |
| | | | | Total: 0.82 |
| | 9 months | 86 | Unknown (RRT 0.20) | 0.12 |
| | | | Unknown (RRT 0.30) | 0.18 |
| | | | Unknown (RRT 0.48) | 0.05 |
| | | | Unknown (RRT 0.64) | 4.09 |
| | | | Unknown (RRT 0.76) | 1.94 |
| | | | Unknown (RRT 0.79) | 0.77 |
| | | | Unknown (RRT 0.89) | 0.27 |
| | | | 10-oxo-DCT | 0.44 |
| | | | 7-epi-DCT | 0.28 |
| | | | 7-epi-10-oxo-DCT | 0.06 |
| | | | | Total: 8.20 |
| | 1 year | 79 | Unknown (RRT 0.20) | 0.37 |
| | | | Unknown (RRT 0.26) | 0.08 |
| | | | Unknown (RRT 0.48) | 0.22 |
| | | | Unknown (RRT 0.64) | 4.76 |
| | | | Unknown (RRT 0.76) | 3.15 |
| | | | Unknown (RRT 0.78) | 0.86 |
| | | | Unknown (RRT 0.89) | 0.56 |
| | | | 10-oxo-DCT | 0.54 |
| | | | 7-epi-DCT | 0.15 |
| | | | | Total: 10.69 |

TABLE 9

Stability of Injection Concentrate Comprising Docetaxel (80 mg/mL), Glycofurol (q.s. to 1 mL), and α-lipoic acid (2 mg/mL)

| Storage Temp. | Time period | % of Initial | Impurity | Peak Area % of Impurities |
|---|---|---|---|---|
| | Initial | 100 | 7-epi-DCT | 0.07 |
| 40° C. | 1 month | 99 | Unknown (RRT 0.87) | 0.06 |
| | | | 10-oxo-DCT | 0.17 |
| | | | 7-epi-DCT | 0.23 |
| | | | | Total: 0.46 |
| | 2 months | 97 | Unknown (RRT 0.63) | 1.07 |
| | | | Unknown (RRT 0.75) | 0.19 |
| | | | Unknown (RRT 0.79) | 0.06 |
| | | | 10-oxo-DCT | 0.25 |
| | | | 7-epi-DCT | 0.20 |
| | | | | Total: 1.77 |
| | 3 months | 93 | Unknown (RRT 0.19) | 0.14 |
| | | | Unknown (RRT 0.28) | 0.05 |
| | | | Unknown (RRT 0.63) | 2.76 |

TABLE 9-continued

Stability of Injection Concentrate Comprising Docetaxel (80 mg/mL), Glycofurol (q.s. to 1 mL), and α-lipoic acid (2 mg/mL)

| Storage Temp. | Time period | % of Initial | Impurity | Peak Area % of Impurities |
|---|---|---|---|---|
| | | | Unknown (RRT 0.75) | 1.10 |
| | | | Unknown (RRT 0.78) | 0.39 |
| | | | Unknown (RRT 0.88) | 0.11 |
| | | | 10-oxo-DCT | 0.35 |
| | | | 7-epi-DCT | 0.42 |
| | | | 7-epi-10-oxo-DCT | 0.07 |
| | | | Total: | 5.39 |
| | 6 months | 88 | Unknown (RRT 0.20) | 0.24 |
| | | | Unknown (RRT 0.37) | 0.12 |
| | | | Unknown (RRT 0.63) | 3.30 |
| | | | Unknown (RRT 0.75) | 5.40 |
| | | | Unknown (RRT 0.88) | 0.61 |
| | | | 10-oxo-DCT | 0.45 |
| | | | 7-epi-DCT | 0.37 |
| | | | 7-epi-10-oxo-DCT | 0.06 |
| | | | Total: | 10.55 |
| 25° C. | 3 months | 99 | Unknown (RRT 0.87) | 0.06 |
| | | | 10-oxo-DCT | 0.13 |
| | | | 7-epi-DCT | 0.16 |
| | | | Total: | 0.35 |
| | 6 months | 98 | Unknown (RRT 0.19) | 0.09 |
| | | | Unknown (RRT 0.63) | 0.19 |
| | | | 10-oxo-DCT | 0.44 |
| | | | 7-epi-DCT | 0.12 |
| | | | 7-epi-10-oxo-DCT | 0.05 |
| | | | Total: | 0.89 |
| | 9 months | 97 | Unknown (RRT 0.20) | 0.06 |
| | | | Unknown (RRT 0.40) | 0.06 |
| | | | Unknown (RRT 0.64) | 0.09 |
| | | | Unknown (RRT 0.71) | 0.05 |
| | | | 10-oxo-DCT | 0.32 |
| | | | 7-epi-DCT | 0.15 |
| | | | 7-epi-10-oxo-DCT | 0.07 |
| | | | Total: | 0.80 |
| | 1 year | 94 | Unknown (RRT 0.20) | 0.09 |
| | | | Unknown (RRT 0.30) | 0.13 |
| | | | Unknown (RRT 0.64) | 2.30 |
| | | | Unknown (RRT 0.76) | 0.60 |
| | | | Unknown (RRT 0.78) | 0.19 |
| | | | Unknown (RRT 0.89) | 0.06 |
| | | | 10-oxo-DCT | 0.40 |
| | | | 7-epi-DCT | 0.12 |
| | | | Total: | 3.89 |

These results show that, in injection concentrates comprising α-lipoic acid at concentrations of about 1 mg/mL and about 2 mg/mL and stored at 40° C. for up to 1 month, the total peak area % of the unknown impurities was reduced as compared to TAXOTERE® or as compared to docetaxel in glycofurol. In injection concentrates comprising α-lipoic acid at a concentration of about 2 mg/mL and stored at 40° C. for 1 month, the peak area % of any individual unknown impurity was not greater than 0.2%. Additionally, in injection concentrates comprising α-lipoic acid at concentrations of about 0.5 mg/mL, about 1 mg/mL, or about 2 mg/mL and stored at 40° C. for up to 3 months, the total peak area % of the known impurities was similar to, or less than, the total peak area % of the known impurities of TAXOTERE® or docetaxel in glycofurol.

Example 4

Applicant prepared an injection concentrate comprising docetaxel (80 mg/mL), glycofurol (q.s. to 1 mL), and α-lipoic acid at a concentration of 5 mg/mL. The injection concentrate was stored at 40° C. for up to 6 months, or 25° C. for up to 1 year, and its stability was assessed using the HPLC method described in Example 2. The results are outlined in Table 10.

TABLE 10

Stability of Injection Concentrate Comprising Docetaxel (80 mg/mL), Glycofurol (q.s. to 1 mL), and α-lipoic acid (5 mg/mL)

| Storage Temp. | Time period | % of Initial | Impurity | Peak Area % of Impurities |
|---|---|---|---|---|
| Initial | | 100 | 7-epi-DCT | 0.06 |
| 40° C. | 1 month | 99 | Unknown (RRT 0.87) | 0.06 |
| | | | 10-oxo-DCT | 0.11 |
| | | | 7-epi-DCT | 0.21 |
| | | | Total: | 0.38 |
| | 2 months | 99 | Unknown (RRT 0.85) | 0.10 |
| | | | 10-oxo-DCT | 0.16 |
| | | | 7-epi-DCT | 0.34 |
| | | | 7-epi-10-oxo-DCT | 0.05 |
| | | | Total: | 0.65 |
| | 3 months | 98 | Unknown (RRT 0.85) | 0.14 |
| | | | 10-oxo-DCT | 0.29 |
| | | | 7-epi-DCT | 0.31 |
| | | | 7-epi-10-oxo-DCT | 0.09 |
| | | | Total: | 0.83 |
| | 6 months | 97 | Unknown (RRT 0.38) | 0.08 |
| | | | Unknown (RRT 0.85) | 0.29 |
| | | | 10-oxo-DCT | 0.15 |
| | | | 7-epi-DCT | 0.57 |
| | | | 7-epi-10-oxo-DCT | 0.09 |
| | | | Total: | 1.18 |
| 25° C. | 3 months | 100 | Unknown (RRT 0.87) | 0.06 |
| | | | 10-oxo-DCT | 0.10 |
| | | | 7-epi-DCT | 0.12 |
| | | | Total: | 0.28 |
| | 6 months | 99 | Unknown (RRT 0.86) | 0.07 |
| | | | 10-oxo-DCT | 0.14 |
| | | | 7-epi-DCT | 0.14 |
| | | | Total: | 0.35 |
| | 9 months | 100 | Unknown (RRT 0.84) | 0.05 |
| | | | 10-oxo-DCT | 0.19 |
| | | | 7-epi-DCT | 0.18 |
| | | | Total: | 0.42 |
| | 1 year | 96 | Unknown (RRT 0.39) | 0.08 |
| | | | Unknown (RRT 0.85) | 0.10 |
| | | | 10-oxo-DCT | 0.27 |
| | | | 7-epi-DCT | 0.28 |
| | | | 7-epi-10-oxo-DCT | 0.07 |
| | | | Total: | 0.80 |

The injection concentrate comprising 5 mg/mL α-lipoic acid generated a reduced total peak area % of the unknown impurities compared to the injection concentrates comprising no α-lipoic acid, or about 0.5 mg/mL, about 1 mg/mL, or about 2 mg/mL α-lipoic acid, or compared to TAXOTERE®.

The injection concentrate comprising about 5 mg/mL α-lipoic acid surprisingly generated no individual unknown impurity having a peak area % greater than 0.2% after storage at 40° C. for up to 3 months or at 25° C. for 1 year. Moreover, in this concentrate, the total peak area % of all impurities generated after storage at 40° C. for 6 months was unexpectedly less than about 1.2%; only a single unknown impurity at about RRT 0.85 showed a peak area % of greater than 0.2%. This impurity was also observed in the TAXOTERE® formulation at a peak area % greater than 0.2%, but after only 3 months storage at 40° C.

Example 5

In consideration of the stability exhibited by the injection concentrate comprising 5 mg/mL α-lipoic acid, other concentrations of α-lipoic acid were also studied. Injection concentrates comprising docetaxel (80 mg/mL), glycofurol (q.s. to 1 mL), and α-lipoic acid at about 4 mg/mL, about 7.5 mg/mL, about 10 mg/mL, and about 20 mg/mL were prepared. The injection concentrates were stored at 40° C. over 1 and/or 2 months, and their stability was assessed using the HPLC method described in Example 2. The results are outlined in Table 11.

TABLE 11

Stability of Injection Concentrate Comprising Docetaxel (80 mg/mL), Glycoftirol (q.s. to 1 mL), and α-lipoic acid (4, 7.5, 10, and 20 mg/mL) after Storage at 40° C.

| Docetaxel Concentration (mg/mL) | Time Period | % of Initial | Impurity | Peak Area % of Impurities |
|---|---|---|---|---|
| 4 mg/mL | Initial | 100 | 10-oxo-DCT | 0.09 |
| | 1 month | 100 | Unknown (RRT 0.63) | 0.27 |
| | | | 10-oxo-DCT | 0.21 |
| | | | Total: | 0.48 |
| | 2 month | 101 | Unknown (RRT 0.63) | 0.72 |
| | | | Unknown (RRT 0.72) | 0.45 |
| | | | 10-oxo-DCT | 0.37 |
| | | | 7-epi-DCT | 0.13 |
| | | | 7-epi-10-oxo-DCT | 0.05 |
| | | | Total: | 1.72 |
| 7.5 mg/mL | Initial | 100 | 10-oxo-DCT | 0.09 |
| | 1 month | 100 | Unknown (RRT 0.63) | 0.06 |
| | | | 10-oxo-DCT | 0.26 |
| | | | 7-epi-DCT | 0.08 |
| | | | 7-epi-10-oxo-DCT | 0.07 |
| | | | Total: | 0.47 |
| 10 mg/mL | Initial | 100 | 10-oxo-DCT | 0.09 |
| | 1 month | 99 | Unknown (RRT 0.63) | 0.10 |
| | | | 10-oxo-DCT | 0.30 |
| | | | 7-epi-DCT | 0.06 |
| | | | 7-epi-10-oxo-DCT | 0.06 |
| | | | Total: | 0.52 |
| 20 mg/mL | Initial | 100 | 7-epi-DCT | 0.07 |
| | 1 month | 99 | Unknown (RRT 0.40) | 0.15 |
| | | | Unknown (RRT 0.64) | 0.35 |
| | | | Unknown (RRT 0.76) | 0.07 |
| | | | Unknown (RRT 0.88) | 0.05 |
| | | | 10-oxo-DCT | 0.32 |
| | | | 7-epi-DCT | 0.10 |
| | | | Total: | 1.04 |
| | 3 months | 97 | Unknown (RRT 0.39) | 0.18 |
| | | | Unknown (RRT 0.64) | 0.47 |
| | | | Unknown (RRT 0.75) | 0.13 |
| | | | Unknown (RRT 0.88) | 0.05 |
| | | | 10-oxo-DCT | 0.55 |
| | | | 7-epi-DCT | 0.13 |
| | | | Total: | 1.51 |
| | 6 months | 92 | Unknown (RRT 0.35) | 1.11 |
| | | | Unknown (RRT 0.47) | 0.13 |
| | | | Unknown (RRT 0.64) | 0.79 |
| | | | Unknown (RRT 0.75) | 0.27 |
| | | | Unknown (RRT 0.88) | 0.06 |
| | | | 10-oxo-DCT | 0.85 |
| | | | 7-epi-DCT | 0.20 |
| | | | 7-epi-10-oxo-DCT | 0.05 |
| | | | Total: | 3.46 |

These results show that, in these injection concentrates after storage at 40° C. for up to 1 month, the total peak area % of the unknown impurities was reduced as compared to TAXOTERE®. In the injection concentrates comprising about 7.5 mg/mL or about 10 mg/mL after storage at 40° C. over 1 month, there was no unknown individual impurity with a peak area % greater than 0.2% as measured by HPLC.

In the injection concentrate comprising 20 mg/mL α-lipoic acid after storage at 40° C. for up to 3 months, the total peak area % of the known impurities was less than the total peak area % of the known impurities of TAXOTERE® or docetaxel in glycofurol without α-lipoic acid. Moreover, the total peak area % of impurities was less than about 2% as measured by HPLC, and the total peak area % of unknown impurities is no greater than about 1% as measured by HPLC after storage at 40° C. over 3 months.

Applicant compared these results to the results generated in the studies of Examples 3 and 4. Applicant discovered that, after storage at 40° C. over 3 months in injection concentrates comprising α-lipoic acid in concentrations of between about 1 mg/mL and about 5 mg/mL, the total peak area % of impurities decreased as the concentration of α-lipoic acid increased. The total peak area % of impurities of the injection concentrate comprising about 5 mg/mL α-lipoic acid was below 2% as measured by HPLC. Similarly, the total peak area % of impurities of the injection concentrate comprising about 20 mg/mL α-lipoic acid was also below 2% as measured by HPLC. Given these data, Applicant concluded that the total peak area % of impurities of injection concentrates comprising between about 5 mg/mL and 20 mg/mL α-lipoic acid would also be below 2% as measured by HPLC.

A similar analysis can be applied to the data for the total peak area % of unknown impurities. Based on the data, Applicant concluded that the total peak area % of unknown impurities of injection concentrates comprising between about 5 mg/mL and 20 mg/mL α-lipoic acid would be below 1% as measured by HPLC.

Taken together, Examples 2-5 suggest that a docetaxel injection concentrate comprising about 5 mg/mL to about 20 mg/mL α-lipoic acid exhibits superior stability as compared to TAXOTERE®.

Example 6

Dihydrolipoic acid, which is the reduced form of α-lipoic acid, was studied in order to determine whether it can similarly improve stability of docetaxel injection concentrates.

Injection concentrates comprising docetaxel (80 mg/mL), glycofurol (q.s. to 1 mL), and dihydrolipoic acid at a concentration of 5 mg/mL were prepared. The injection concentrates were stored at 40° C. over 1, 2, or 3 months, or 25° C. for 6 months. The stability of the injection concentrates was assessed using the HPLC method described in Example 2. The results are outlined in Table 12.

TABLE 12

Stability of Injection Concentrates Comprising Docetaxel (80 mg/mL), Glycofurol (q.s. to 1 mL), and Dihydrolipoic acid (5 mg/mL)

| Storage Temp. | Time period | % of Initial | Impurity | Peak Area % of Impurities |
|---|---|---|---|---|
| | Initial | 100 | None | N/A |
| 40° C. | 1 month | 100 | Unknown (RRT 0.35) | 0.08 |
| | | | Unknown (RRT 0.50) | 0.74 |
| | | | Unknown (RRT 0.63) | 0.20 |
| | | | Unknown (RRT 0.75) | 0.12 |
| | | | Total: | 1.14 |
| | 2 months | 100 | Unknown (RRT 0.35) | 0.08 |
| | | | Unknown (RRT 0.47) | 0.60 |
| | | | Unknown (RRT 0.50) | 0.28 |
| | | | Unknown (RRT 0.63) | 0.45 |
| | | | Unknown (RRT 0.75) | 0.24 |
| | | | Total: | 1.65 |
| | 3 months | 93 | Unknown (RRT 0.23) | 0.34 |
| | | | Unknown (RRT 0.35) | 0.67 |
| | | | Unknown (RRT 0.63) | 0.56 |
| | | | Unknown (RRT 0.75) | 0.30 |
| | | | Unknown (RRT 1.29) | 0.25 |
| | | | Unknown (RRT 1.32) | 0.08 |
| | | | 7-epi-DCT | 0.10 |
| | | | 10-oxo-DCT | 0.64 |
| | | | Total: | 2.94 |
| 25° C. | 6 months | 99 | Unknown (RRT 0.39) | 0.82 |
| | | | Unknown (RRT 0.63) | 0.24 |
| | | | Unknown (RRT 0.75) | 0.18 |
| | | | Unknown (RRT 1.32) | 0.06 |
| | | | 7-epi-DCT | 0.06 |
| | | | Total: | 1.36 |

Dihydrolipoic acid also provides a viable alternative to formulating docetaxel without polysorbates or polyethoxylated castor oil solubilizers. In the presence of dihydrolipoic acid, the total peak area % of impurities was less than about 2%, and an insignificant amount of % of initial concentration was affected at 40° C. after 30 days.

However, compared to α-lipoic acid, dihydrolipoic acid provides less of a stabilization effect for docetaxel during storage. For example, dihydrolipoic acid did not reduce the total peak area % of unknown impurities as compared to TAXOTERE® or as compared to injection concentrates comprising docetaxel and glycofurol without α-lipoic acid.

Example 7

The stabilizing effects of α-lipoic acid were studied in injection concentrates comprising solubilizers other than glycofurol. In particular, stability was assessed in injection concentrates comprising ethanol.

An injection concentrate comprising docetaxel (80 mg/mL), ethanol (q.s. to 1 mL), and α-lipoic acid (5 mg/mL) was prepared. The injection concentrate was stored at 40° C. over 1 month, and its stability, which was assessed using the HPLC method described in Example 2, was compared to the stability of an injection concentrate comprising docetaxel (80 mg/mL) and ethanol (q.s. to 1 mL). These results are outlined in Table 13.

TABLE 13

Stability of Injection Concentrate Comprising Docetaxel (80 mg/mL), Ethanol (q.s. to 1 mL), and α-lipoic acid (5 mg/mL)

| Formulation | Storage Condition | % of Initial | Impurity | Peak Area % of Impurities |
|---|---|---|---|---|
| Docetaxel (80 mg/mL) Ethanol (q.s. 1 mL) | Initial | 100 | 10-oxo-DCT 7-epi-DCT | 0.08 0.06 Total: 0.14 |
|  | 40° C. 1 month | 98 | Unknown (RRT 0.21) Unknown (RRT 0.25) Unknown (RRT 0.72) 10-oxo-DCT 7-epi-DCT 7-epi-10-oxo-DCT | 0.10 0.06 0.07 1.03 0.58 0.50 Total: 2.34 |
| Docetaxel (80 mg/mL) Ethanol (q.s. 1 mL) α-lipoic acid | Initial | 100 | 10-oxo-DCT | 0.08 |
|  | 40° C. 1 month | 100 | 10-oxo-DCT 7-epi-DCT 7-epi-10-oxo-DCT | 0.08 0.32 0.06 Total: 0.46 |

The results indicate that the inclusion of α-lipoic acid in an injection concentrate comprising docetaxel and ethanol stabilizes the injection concentrate. In particular, this injection concentrate reduces the generation of known degradants 10-oxo-DCT, 7-epi-DCT, and 7-epi-10-oxo-DCT, as well as unknown impurities.

Example 8

The physical properties of the injection concentrate were also assessed. An injection concentrate comprising docetaxel (80 mg/mL), glycofurol (q.s. to 1 mL), and α-lipoic acid at a concentration of 5 mg/mL was prepared. The injection concentrate then underwent aseptic sterilization.

The injection concentrate was a clear and colorless solution. The particulate matter content met U.S. Pharmacopeia (USP) standards, which requires not more than 6000 particles that are larger than 10 μm and not more than 600 particles that are greater than 25 μm; the injection concentrate contained only 26 particles greater than 10 μm and 5 particles greater than 25 μm. Further, the injection concentrate also met USP requirements for sterility and bacterial endotoxin content (less than 0.25 EU/mg, which meets the USP requirement of less than 2.33 EU/mg).

Example 9

An initial diluted solution was prepared according to an embodiment of the invention to assess its physical properties and stability. An injection concentrate comprising docetaxel (80 mg/mL), glycofurol (q.s. to 1 mL), and α-lipoic acid (5 mg/mL) was prepared. The injection concentrate was mixed with a diluent comprising TPGS 1000 (1.5 g), PEG 400 (2.5 mL), NaCl (72 mg), and water (q.s. to 7 mL). The resulting initial diluted solution comprised 10 mg/mL of docetaxel, 187.5 mg/mL of TPGS 1000, 13.5 mg/mL of glycofurol (density 1.08 g/mL), and 343.75 mg/mL of PEG 400 (density 1.1 g/mL). The initial diluted solution then underwent aseptic sterilization.

The initial diluted solution was a clear, colorless, viscous solution. The particulate matter content met USP standards, as there were only 71 particles greater than 10 μm and 14 particles greater than 25 μm. Sterility and bacterial endotoxin content also met USP standards.

The initial diluted solution was stored at room temperature for 8 or 24 hours, and its stability was assessed using the HPLC method described in Example 2. The stability data are presented in Table 14.

TABLE 14

Stability and Physical Appearance of Initial Diluted Solution After Storage at Room Temperature.

| Time Period | % of Initial | Peak Area % of Impurities | Physical Appearance. |
|---|---|---|---|
| Initial | 100 | BDL | Clear solution |
| 8 hrs | 100 | BDL | Clear solution |
| 24 hrs | 99 | BDL | Clear solution |

BDL: Below Detection Limit

The results indicate that the initial diluted solution does not generate any detectable impurities and does not form any precipitates after 24 hours at room temperature. By comparison, the initial dilution of TAXOTERE® (docetaxel, polysorbate 80, ethanol) may be stored in the refrigerator or at room temperature for no more than 8 hours. See TAXOTERE® Prescribing Information.

Example 10

A final dilution for infusion was prepared according to an embodiment of the invention to assess its stability. An injection concentrate comprising docetaxel (80 mg/mL), glycofurol (q.s. to 1 mL), and α-lipoic acid (5 mg/mL) was prepared. The injection concentrate was mixed with a diluent comprising TPGS 1000 (1.5 g), PEG 400 (2.5 mL), NaCl (72 mg), and water (q.s. to 7 mL) to form an initial diluted solution. The initial diluted solution was diluted with normal saline to form a final dilution for infusion containing docetaxel at a concentration of either 0.32 or 0.74 mg/mL. The final dilution for infusion was stored at room temperature for 0-8 hours, and its stability was assessed using the HPLC method described in Example 2. The stability data are presented in Tables 15 and 16.

TABLE 15

Stability and Physical Appearance of Final Dilution
for Infusion Comprising 0.32 mg/mL
Docetaxel After Storage at Room Temperature.

| Time Period | % of Initial | Peak Area % of Impurities | Physical Appearance |
|---|---|---|---|
| Initial | 100 | BDL | Clear solution |
| 1 hr | 100 | BDL | Clear solution |
| 2 hrs | 100 | BDL | Clear solution |
| 3 hrs | 100 | BDL | Clear solution |
| 4 hrs | 100 | BDL | Clear solution |
| 5 hrs | 100 | BDL | Clear solution |
| 6 hrs | 100 | BDL | Clear solution |
| 7 hrs | 100 | BDL | Clear solution |
| 8 hrs | 100 | BDL | Clear solution |

BDL: Below Detection Limit

TABLE 16

Stability and Physical Appearance of Final Dilution
for Infusion Comprising 0.74 mg/mL Docetaxel
After Storage at Room Temperature.

| Time Period | % of Initial | Peak Area % of Impurities | Physical Appearance |
|---|---|---|---|
| Initial | 100 | BDL | Clear solution |
| 1 hr | 100 | BDL | Clear solution |
| 2 hrs | 100 | BDL | Clear solution |
| 3 hrs | 100 | BDL | Clear solution |
| 4 hrs | 100 | BDL | Clear solution |
| 5 hrs | 100 | BDL | Clear solution |
| 6 hrs | 100 | BDL | Clear solution |
| 7 hrs | 100 | BDL | Clear solution |
| 8 hrs | 99 | BDL | Clear solution |

These results show that the final dilution for infusion comprising docetaxel at either 0.32 or 0.74 mg/mL is physically and chemically stable for at least 8 hours under ambient storage conditions. Notably, the final diluted solution for infusion of TAXOTERE® is physically stable for only 4 hours. See TAXOTERE® Prescribing Information.

Example 11

Table 17 illustrates formulations for a single-vial presentation of docetaxel in the concentrations of about 10 mg/mL to about 20 mg/mL.

TABLE 17

Various Formulations for the Single-Vial Presentation

| Docetaxel (mg) | Docetaxel (mg/mL) | TPGS 1000 (g) | α-Lipoic acid (mg/mL) | Glycofurol (mL) | PEG 400 (mL) |
|---|---|---|---|---|---|
| 80 | 16 | 1.5 | 5 | 1 | ~2.5 |
| 100 | 20 | 1.875 | 6.25 | 1.25 | ~1.9 |
| 100 | 10 | 1.875 | 6.25 | 1.25 | ~6.9 |
| 100 | 20 or 10 | 1.875 | 12.5 | 1.25 | ~1.9 or ~6.9 |
| 100 | 20 or 10 | 1.875 | 25 | 1.25 | ~1.9 or ~6.9 |
| 100 | 20 or 10 | 1.875 | 50 | 1.25 | ~1.9 or ~6.9 |
| 100 | 20 or 10 | 1.875 | 100 | 1.25 | ~1.9 or ~6.9 |

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention.

What is claimed is:

1. A pharmaceutical formulation for use in treatment of a patient in need thereof, comprising:
   (a) docetaxel, or a pharmaceutically acceptable salt thereof, in an amount of about 40 mg/mL to about 80 mg/mL;
   (b) glycofurol; and
   (c) α-lipoic acid, or a pharmaceutically acceptable salt thereof, in an amount of about 1 mg/mL to about 10 mg/mL;
   wherein the formulation is substantially free of polysorbates and polyethoxylated castor oil.

2. The formulation of claim 1, wherein docetaxel, or a pharmaceutically acceptable salt thereof, is in an amount of about 80 mg/mL.

3. The formulation of claim 1, wherein α-lipoic acid, or a pharmaceutically acceptable salt thereof, is in an amount of about 5 mg/mL.

4. The formulation of claim 1, wherein α-lipoic acid, or a pharmaceutically acceptable salt thereof, is in an amount of about 1 mg/mL, about 2 mg/mL, or about 5 mg/mL.

5. The formulation of claim 1, wherein α-lipoic acid, or a pharmaceutically acceptable salt thereof, is in an amount of about 1 mg/mL to about 5 mg/mL.

6. A pharmaceutical formulation for use in treatment of a patient in need thereof, comprising a combination of:
   (a) docetaxel, or a pharmaceutically acceptable salt thereof, in an amount of about 40 mg/mL to about 80 mg/mL;
   (b) glycofurol;
   (c) α-lipoic acid, or a pharmaceutically acceptable salt thereof, in an amount of about 1 mg/mL to about 10 mg/mL; and
   (d) a diluent;
   wherein the formulation is substantially free of polysorbates and polyethoxylated castor oil.

7. The formulation of claim 6, wherein the diluent comprises at least one hydrotrope.

8. The formulation of claim 7, wherein the hydrotrope is selected from a group consisting of tocopherol polyethylene glycol succinate ("TPGS"), polyethylene glycol ("PEG") 400, and a combination thereof.

9. The formulation of claim 8, comprising about 1.5 grams TPGS, about 2.5 mL PEG 400, and further comprising about 72 mg sodium chloride.

10. The formulation of claim 9, wherein docetaxel is in an amount of about 0.32 mg/mL to 0.74 mg/mL after final dilution with saline, dextrose or water, and wherein after about 8 hours at room temperature the physical appearance of the formulation is clear.

11. A package comprising:
   (a) a pharmaceutical formulation comprising
      i. docetaxel, or a pharmaceutically acceptable salt thereof, in an amount of about 40 mg/mL to about 80 mg/mL;
      ii. glycofurol;
      iii. α-lipoic acid, or a pharmaceutically acceptable salt thereof, in an amount of about 1 mg/mL to about 10 mg/mL; and
   (b) a diluent;
   wherein the pharmaceutical formulation and the diluent are substantially free of polysorbates and polyethoxylated castor oil.

12. The package of claim 11, wherein the diluent comprises tocopherol polyethylene glycol succinate (TPGS), polyethylene glycol (PEG), or both TPGS and PEG.

13. The package of claim 11, wherein
the pharmaceutical formulation comprises docetaxel in an amount of about 80 mg; α-lipoic acid in an amount of about 5 mg; and glycofurol in an amount sufficient to bring the volume of the pharmaceutical formulation to about 1 mL; and
(ii) the diluent comprises tocopherol polyethylene glycol succinate (TPGS) in an amount of about 1.5 g, polyethylene glycol 400 in an amount of about 2.5 mL, sodium chloride in an amount of about 72 mg, and water in an amount sufficient to bring the diluent volume to about 7 mL.

14. The formulation of claim 1, wherein docetaxel, or a pharmaceutically acceptable salt thereof, is in an amount of about 40 mg/mL.

15. The formulation of claim 1, wherein the total peak area % of unknown impurities in said formulation is less than total peak area % of unknown impurities of a formulation without α-lipoic acid, as measured by high performance liquid chromatography after storage at 40° C. over 1 month.

16. The pharmaceutical formulation of claim 9, further comprising citric acid.

17. The formulation of claim 3, wherein the total peak area % of unknown impurities in said formulation is less than total peak area % of unknown impurities of a formulation without α-lipoic acid as measured by high performance liquid chromatography after storage at 40° C. over 3 months.

18. The formulation of claim 1, further comprising ethanol.

19. The formulation of claim 2, wherein α-lipoic acid, or a pharmaceutically acceptable salt thereof, is in an amount of about 5 mg/mL.

20. The formulation of claim 14, wherein α-lipoic acid, or a pharmaceutically acceptable salt thereof, is in an amount of about 5 mg/mL.

\* \* \* \* \*